US011701564B2

(12) United States Patent
Seitz et al.

(10) Patent No.: US 11,701,564 B2
(45) Date of Patent: Jul. 18, 2023

(54) SYSTEM FOR DETERMINING A GAME SCENARIO IN A SPORTS GAME

(71) Applicants: Fraunhofer-Gesellschaft zur Foerderung der angewandten Forschung e.V., Munich (DE); Next11 Technologies, Copenhagen (DK)

(72) Inventors: Jochen Seitz, Erlangen (DE); Birendra Ghimire, Erlangen (DE); Sebastian Kram, Erlangen (DE); Nikolaj Thomassen, Kopenhagen (DK); Sylvie Couronné, Erlangen (DE)

(73) Assignees: Fraunhofer-Gesellschaft zur Foerderung der angewandten Forschung e.V., Munich (DE); NEXT11 TECHNOLOGIES, Copenhagen N (DK)

( * ) Notice: Subject to any disclaimer, the term of this patent is extended or adjusted under 35 U.S.C. 154(b) by 0 days.

(21) Appl. No.: 17/108,756

(22) Filed: Dec. 1, 2020

(65) Prior Publication Data

US 2021/0077886 A1 Mar. 18, 2021

Related U.S. Application Data

(63) Continuation of application No. PCT/EP2019/063886, filed on May 28, 2019.

(30) Foreign Application Priority Data

Jun. 1, 2018 (EP) .................................... 18175616

(51) Int. Cl.
*A63B 71/06* (2006.01)

(52) U.S. Cl.
CPC .................................. *A63B 71/06* (2013.01)

(58) Field of Classification Search
CPC ..................................................... A63B 71/06
See application file for complete search history.

(56) References Cited

U.S. PATENT DOCUMENTS 7,040,998 B2 * 5/2006 Jolliffe .............. A63B 24/0021 473/151
9,317,660 B2 4/2016 Burich et al.
(Continued)

FOREIGN PATENT DOCUMENTS

EP 2016425 B1 6/2011
EP 2682052 A2 1/2014
(Continued)

OTHER PUBLICATIONS

"Goaltime—Equipement connecté pour le football", URL: https://goaltime.fr/.
(Continued)

*Primary Examiner* — Reginald A Renwick
(74) *Attorney, Agent, or Firm* — Perkins Coie LLP; Michael A. Glenn

(57) ABSTRACT

The invention concerns a method and a system for determining a game scenario in a sports game, the system including a player module being attachable to a player, an equipment module being attachable to a sports equipment to be used in the sports game, and a computing unit. The computing unit may be configured to receive player based data from the player module and equipment based data from the equipment module, the player based data representing an activity profile of the player and the equipment based data representing a motion profile of the equipment. The computing unit may further be configured to determine, based on the activity profile of the player and on the motion profile of the equipment, one of a plurality of game scenarios involving the player and the equipment.

13 Claims, 18 Drawing Sheets

(56) References Cited

U.S. PATENT DOCUMENTS

| | | | | |
|---|---|---|---|---|
| 2010/0283630 | A1 | 11/2010 | Alonso | |
| 2014/0002664 | A1 * | 1/2014 | Hanabusa | H04N 5/04 348/159 |
| 2015/0018111 | A1 * | 1/2015 | Nadkarni | A63B 69/3632 473/223 |
| 2015/0062440 | A1 | 3/2015 | Baxter et al. | |
| 2016/0001136 | A1 | 1/2016 | King et al. | |
| 2016/0114487 | A1 | 4/2016 | Lacaze et al. | |
| 2016/0310820 | A1 * | 10/2016 | Kline | G06F 3/00 |
| 2017/0189756 | A1 * | 7/2017 | Brothers | A63B 24/0006 |
| 2019/0347956 | A1 * | 11/2019 | Daga | G16H 40/67 |

FOREIGN PATENT DOCUMENTS

| | | | |
|---|---|---|---|
| EP | 2765551 | A1 | 8/2014 |
| EP | 2370186 | B1 | 1/2015 |
| JP | 2016202890 | A | 12/2016 |
| WO | 2012112900 | A1 | 8/2012 |
| WO | 2013166456 | A2 | 11/2013 |
| WO | 2014008134 | A1 | 1/2014 |
| WO | 2015169915 | A1 | 11/2015 |
| WO | 2017011811 | A1 | 1/2017 |
| WO | 2017040242 | A1 | 3/2017 |
| WO | 2017111933 | A1 | 6/2017 |

OTHER PUBLICATIONS

"M-station, Munin Sports", URL: https://muninsports.com/us/.

Fraunhofer IIS/Kurt Fuchs, "Measurement System for Respiratory Frequency and Effort Integrated Directly in Clohes", RespiSHIRT®, URL: https://www.iis.fraunhofer.de/de/ff/sse/health/medical-sensors-and-analytics/prod/respishirt.html.

Fraunhofer IIS, "RedFIR®", URL: https://www.iis.fraunhofer.de/de/ff/lv/lok/tech/redfir.html.

Hönig, Wolfgang, et al., "RF-Based Relative Localization for Robot Swarms", URL: http://www-scf.usc.edu/~nkamra/pdf/locrobot.pdf.

Paulsson, Märta, "High-Level Control of UAV Swarms with RSSI Based Position Estimation", URL: https://pdfs.semanticscholar.org/785c/2e56c84b46226f6ab9b9ee77d8831ee1f0e0.pdf.

Pricone, M, et al., "A heterogeneous RSSI-based localization system for indoor and outdoor sports activities", 2014 International Wireless Communications and Mobile Computing Conference (IWCMC), Nicosia, URL: https://ieeexplore.ieee.org/stamp/stamp.jsp?tp=&arnumber=6906369, pp. 274-280.

* cited by examiner

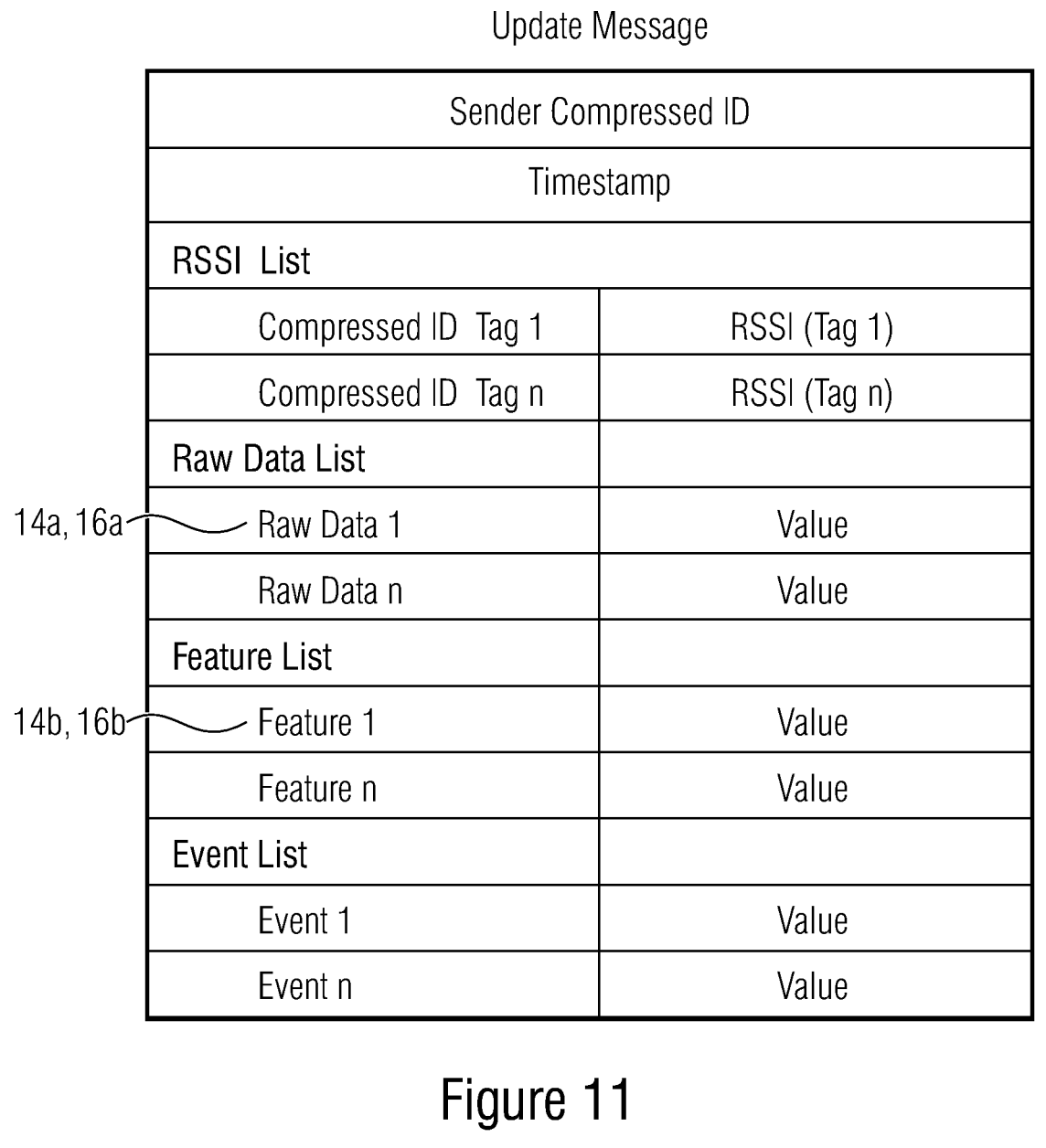

Update Message

| Sender Compressed ID | |
|---|---|
| Timestamp | |
| RSSI List | |
| Compressed ID Tag 1 | RSSI (Tag 1) |
| Compressed ID Tag n | RSSI (Tag n) |
| Raw Data List | |
| Raw Data 1 | Value |
| Raw Data n | Value |
| Feature List | |
| Feature 1 | Value |
| Feature n | Value |
| Event List | |
| Event 1 | Value |
| Event n | Value |

Figure 11

SYSTEM FOR DETERMINING A GAME SCENARIO IN A SPORTS GAME

CROSS-REFERENCES TO RELATED APPLICATIONS

This application is a continuation of copending International Application No. PCT/EP2019/063886, filed May 28, 2019, which is incorporated herein by reference in its entirety, and additionally claims priority from European Application No. EP 18 175 616.4, filed Jun. 1, 2018, which is incorporated herein by reference in its entirety.

The present invention is concerned with determining at least one of a plurality of game scenarios during a sports game. Embodiments of the present invention relate to a system for determining a game scenario, and in particular for performing sports analytics with cooperative sensor modules for the players of the sports game and for a sports equipment to be used in said sports game.

BACKGROUND OF THE INVENTION

Sports games, and in particular team sports games like soccer, football, baseball, basketball and the like, are very popular and attract a lot of people nowadays. Statistics gathered during a match, or even during a training session, may be of particular interest for trainers but also for spectators and commentators and, of course, the players themselves. A lot of information may be obtained by means of such statistical analytics.

For example, in a soccer match a lot of different game events and game scenarios may exist, for instance, playing a pass from player A to player B, ball possession of a team, duels between two players, shots at the goal, and many more. To take up the above examples, these game scenarios may be statistically evaluated in order to gather information about, for example, a number of successful or unsuccessful passes, a percentage of ball possession, won or lost duels, number of shots at the goal, and the like. These statistics may be set up for single individual players or for the entire team.

In the present disclosure, a game event may be an event which happens during a match and in which one entity, for example an individual player or an individual ball, is involved. A game scenario in turn may be a scenario that may be related with said game, which happens during said game and in which at least two entities, and in particular a player of the game and a sports equipment used in said game, are commonly involved.

In order to set up the above mentioned game relevant statistics, game-related events and/or scenarios may usually have to be determined and counted. In known technology, a lot of concepts may exist for determining single game events or game scenarios.

For example, US 2010/283,630 A1 suggests equipping football players and the football itself with sensors for measuring, e.g. speed, acceleration and impact of each player and/or the ball. Furthermore, the sensors allow to track the players and the ball inside the game field. Tracking may be performed by means of Real Time Locating Systems (RTLS) or Real Time Sensing Systems (RTSS). This system further uses video systems for capturing the match, wherein the sensor data may be superimposed on the video footage. This allows a visual allocation of the sensor data to the corresponding player wearing the respective sensor. For example, the actual speed of a player running over the game field may be graphically displayed in real time on the screen. This system may allow for a convenient determination of game events and it may be highly attractive to users due to its real time imaging capability. However, systems like these are very complex and thus very expensive. Furthermore, since two different technical solutions, namely video imaging and RF communication, are used in common, malfunction of one of these two devices would lead to a failure of the entire system.

WO 2015/169 915 A1 suggests a simpler approach. It describes a method and a device for detecting a ball kick by simply attaching a sensor device to a leg or a foot of a player. The sensor device may comprise a rotation sensor and a microphone. The rotation sensor detects a rotation of the player's foot thereby estimating that the ball has been kicked. However, distinction between a ball kick and, e.g. stomping on the ground or unintentionally kicking into the grass, is difficult. Thus, it is described to detect the sound that appears upon kicking the ball by means of the microphone. However, in situations where two or more players are positioned close to each other, e.g. in duels, it may become very difficult to exactly detect which one of the two or more players may have recently kicked the ball.

A further conventional system is known under the name RedFIR®. This system is based on ultra high precision positioning detection of the players and the ball. The players and the ball are equipped with a transmitter by means of which the position of the players and the ball can be detected with a resolution in the range of centimeters. This may even allow a distinct position detection between the left leg and the right leg of the player. However, systems like these which use high precision positioning detection tend to be expensive, which may therefore be interesting for the professional sports rather than for private or amateur players.

SUMMARY

According to an embodiment, a system for determining a game scenario in a sports game may have: a player module being attachable to a player, an equipment module being attachable to a sports equipment to be used in said sports game, and a computing unit for receiving player based data from the player module and equipment based data from the equipment module, the player based data representing an activity profile of the player and the equipment based data representing a motion profile of the equipment, wherein the player module includes a player sensor device configured to provide raw measurement data associated with the player to which the player module is attached, wherein the player module is configured to perform a feature extraction of the raw measurement data for determining, based on one or more extracted features, one or more physical events being executable by the player, wherein the player module is configured to determine the activity profile of the player based on the extracted one or more features and/or based on the determined one or more physical events, and to transmit the activity profile as the player based data to the computing unit, and/or to transmit the extracted one or more features and/or the determined one or more physical events to the computing unit for determining the activity profile of the player, and wherein the equipment module includes an equipment sensor device configured to provide raw measurement data associated with the equipment to which the equipment module is attached, wherein the equipment module is configured to perform a feature extraction of the raw measurement data for determining, based on one or more extracted features, one or more physical events being executable by or exertable on the equipment, wherein the equipment module is configured to determine the motion profile of the equipment based on the extracted one or more features and/or based on the determined one or more physical events, and to transmit the motion profile as the equipment based data to the computing unit, and/or to transmit the extracted one or more features and/or the determined one or more physical events to the computing unit for determining the motion profile of the equipment, and wherein the computing unit includes a Game Scenario Classification Stage that is configured to classify the activity profile of the player and the motion profile of the equipment into one of a plurality of game scenarios involving the player and the equipment.

According to an embodiment, a method for determining a game scenario in a sports game may have the steps of: receiving player based data from a player module being attached to a player, the player based data representing an activity profile of the player, receiving equipment based data from an equipment module being attached to a sports equipment to be used in said sports game, the equipment based data representing a motion profile of the equipment, wherein receiving player based data from the player module includes receiving raw measurement data from a player sensor device included in the player module, the raw measurement data being associated with the player to which the player module is attached, and performing a feature extraction of the raw measurement data for determining, based on one or more extracted features, one or more physical events being executable by the player, determining the activity profile of the player based on the extracted one or more features and/or based on the determined one or more physical events and transmitting the activity profile as the player based data to the computing unit, and/or transmitting the extracted one or more features and/or the determined one or more physical events to the computing unit for determining the activity profile of the player, and wherein receiving equipment based data from the equipment module includes receiving raw measurement data from an equipment sensor device included in the equipment module, the raw measurement data being associated with the equipment to which the equipment module is attached, and performing a feature extraction of the raw measurement data for determining, based on one or more extracted features, one or more physical events being executable by or exertable on the equipment, determining the motion profile of the equipment based on the extracted one or more features and/or based on the determined one or more physical events and transmitting the motion profile as the equipment based data to the computing unit, and/or transmitting the extracted one or more features and/or the determined one or more physical events to the computing unit for determining the motion profile of the equipment, and classifying the activity profile of the player and the motion profile of the equipment into one of a plurality of game scenarios involving the player and the equipment.

Another embodiment may have a non-transitory digital storage medium having a computer program stored thereon to perform the method for determining a game scenario in a sports game, the method including receiving player based data from a player module being attached to a player, the player based data representing an activity profile of the player, receiving equipment based data from an equipment module being attached to a sports equipment to be used in said sports game, the equipment based data representing a motion profile of the equipment, wherein receiving player based data from the player module includes receiving raw measurement data from a player sensor device included in the player module, the raw measurement data being associated with the player to which the player module is attached, and performing a feature extraction of the raw measurement data for determining, based on one or more extracted features, one or more physical events being executable by the player, determining the activity profile of the player based on the extracted one or more features and/or based on the determined one or more physical events and transmitting the activity profile as the player based data to the computing unit, and/or transmitting the extracted one or more features and/or the determined one or more physical events to the computing unit for determining the activity profile of the player, and wherein receiving equipment based data from the equipment module includes receiving raw measurement data from an equipment sensor device included in the equipment module, the raw measurement data being associated with the equipment to which the equipment module is attached, and performing a feature extraction of the raw measurement data for determining, based on one or more extracted features, one or more physical events being executable by or exertable on the equipment, determining the motion profile of the equipment based on the extracted one or more features and/or based on the determined one or more physical events and transmitting the motion profile as the equipment based data to the computing unit, and/or transmitting the extracted one or more features and/or the determined one or more physical events to the computing unit for determining the motion profile of the equipment, and classifying the activity profile of the player and the motion profile of the equipment into one of a plurality of game scenarios involving the player and the equipment, when said computer program is run by a computer.

A first aspect concerns, a system for determining a game scenario in a sports game. The system may comprise a player module being attachable to a player, an equipment module being attachable to a sports equipment that is to be used in said sports game, and a computing unit. The computing unit is configured to receive player based data from the player module and equipment based data from the equipment module. The player based data may represent an activity profile of the player and the equipment based data may represent a motion profile of the equipment. According to the invention, the computing unit is configured to determine, based on the activity profile of the player and on the motion profile of the equipment, one of a plurality of game scenarios involving the player and the equipment.

A second aspect concerns a method for determining a game scenario in a sports game. The method comprising a step of receiving player based data from a player module being attached to a player, wherein the player based data may represent an activity profile of the player. The method further comprises a step of receiving equipment based data from an equipment module being attached to a sports equipment to be used in said sports game, wherein the equipment based data may represent a motion profile of the equipment. According to the invention, the method comprises a further step of determining, based on the activity profile of the player and on the motion profile of the equipment, one of a plurality of game scenarios involving the player and the equipment.

According to a third aspect, computer programs are provided, wherein each of the computer programs is configured to implement the above-described method when being executed on a computer or signal processor, so that the above-described method is implemented by one of the computer programs.

Accordingly, the inventive concept may suggest to put a module in the sports equipment, e.g. a ball, and to provide player modules, too. In contrast to known technology it becomes possible to reliably detect a game scenario in which at least the sports equipment and the player are involved. For example, a game scenario "Pass from a first player to a second player" in a soccer game may be determined in that it can be reliably detected that a first player kicked the ball, that the ball has been kicked by said first player and that a second player accepted the ball. It may even be determined whether the pass that was played was a high pass or a low pass, whether the ball has arrived at a player of the same team so as to be classified as a successful pass, whether the ball has arrived at a player of the opposing team so as to be classified as an unsuccessful pass, and many more. According to the invention, this may be done by determining an activity profile of a player and a motion profile of the ball in real-time and to link, e.g. to combine or fuse, the activity profile of the player with the motion profile of the ball. By doing so, a very reliable and robust association between the ball and the player who is currently handling the ball becomes possible, whereas simple and thus cheap modules may be deployed. In some examples of the invention it may be possible to determine the activity profile of the player and the motion profile of the ball solely with acceleration sensors or Inertial Measurement Units (IMUs). Combining these information the estimation of passes from a first player to a second player, for example, will be of much higher accuracy than using e.g. just a player module, and much cheaper than using precise positioning. It is easier to distinguish successful and unsuccessful passes even if more players and balls are involved, like in a training scenario.

BRIEF DESCRIPTION OF THE DRAWINGS

Embodiments of the present invention will be detailed subsequently referring to the appended drawings, in which:

FIG. 11 shows an example of a content of a message in which player based data and equipment based data may be transferred from the player module/equipment module to the computing unit according to an embodiment;

DETAILED DESCRIPTION OF THE INVENTION

Figure 1:
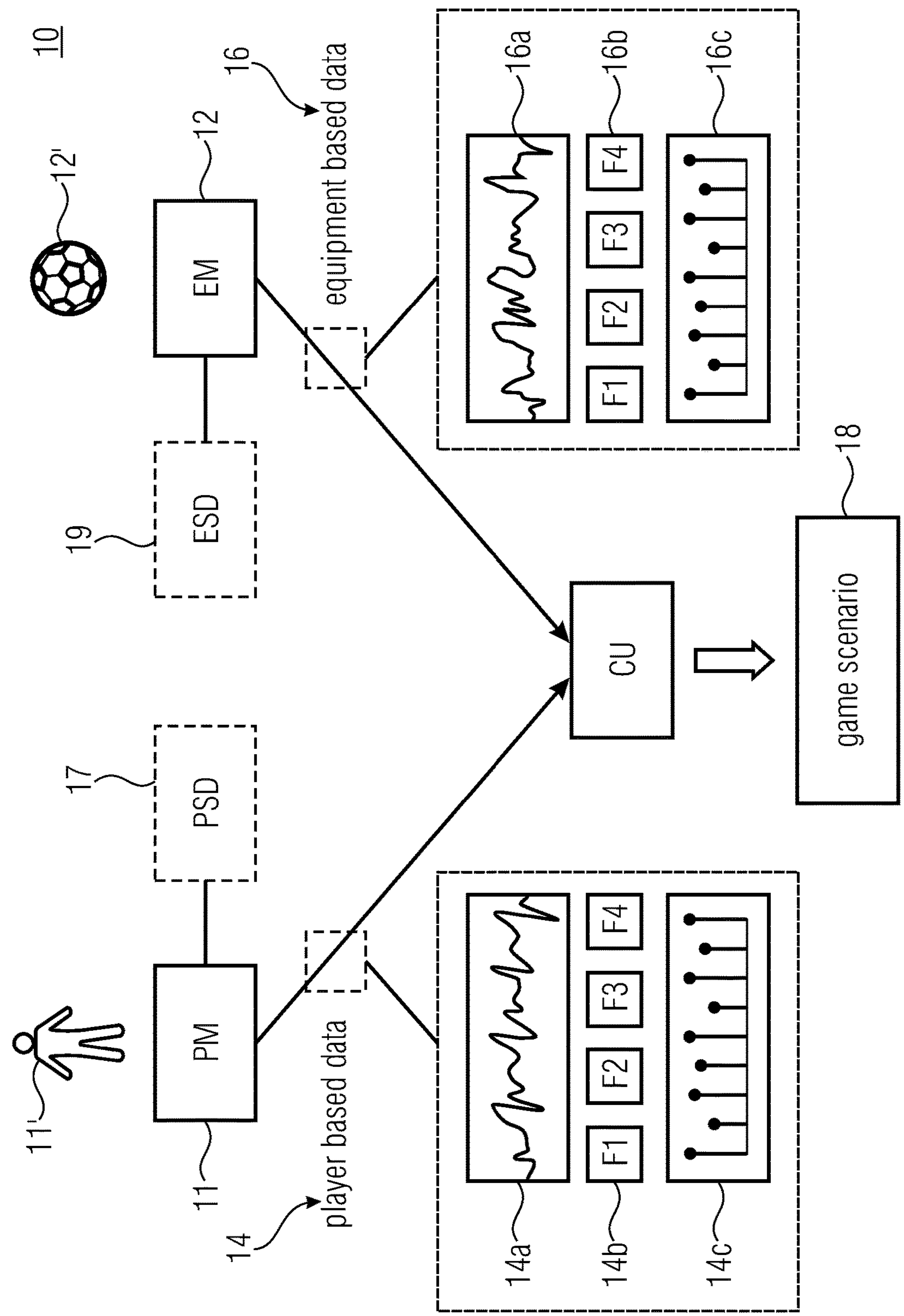
FIG. 1 shows a schematic overview of an inventive system according to an embodiment.

Equal or equivalent elements or elements with equal or equivalent functionality are denoted in the following description by equal or equivalent reference numerals.

In order to exemplarily illustrate the inventive concept, soccer may be described as a non-limiting example of a sports game. Accordingly, a soccer player may be described as a non-limiting example of a player, a ball may be described as a non-limiting example of an equipment. Thus, a ball module may be described as a non-limiting example for an equipment module. Furthermore, a so-called tag may be described as a non-limiting example for a module, i.e. a player module and/or an equipment module.

Instead of soccer, various other sports games may be imaginable in which the present inventive concept may be deployed, for example, tennis, football, baseball, basketball, cricket and many more. The inventive concept may advantageously be used in team sports comprising a plurality of players. Each player may advantageously be equipped with at least one player module.

However, the inventive concept may also be used for a single player, for example during training. According to the inventive concept, an equipment module may be attached to an equipment or to each of a plurality of equipments that may be used during a particular sports game. For instance, in racket sports, an equipment module may be attached to a racket (tennis racket, baseball bat, golf club, etc.) and/or an equipment module may be attached to a ball, puck and the like.

The inventive system may be used in order to determine a game scenario of the respective game during a match and/or during training.

The inventive system may provide each of the herein described data, e.g. player based data and/or equipment based data and/or RSSI measurement data in real-time, i.e. with a delay of no more than three seconds, and advantageously with a delay of only a few milliseconds. This may allow a real-time visualization of the data that may be processed by the inventive system. For example, a trainer may watch the data and/or the game scenarios that may be determined by the inventive system in real time while the players are playing the game, be it during a match or during a training session.

FIG. 1 shows a system 10 for determining a game scenario in a sports game according to an exemplary embodiment.

The system 10 may comprise a player module 11 being attachable to a player 11' and an equipment module 12 being attachable to a sports equipment 12' to be used in said sports game.

The system 10 may further comprise a computing unit 13 for receiving player based data 14 from the player module 11 and equipment based data 16 from the equipment module 12. The player based data 14 may represent an activity profile of the player 11' and the equipment based data 16 may represent a motion profile of the equipment 12'.

The player module 11 may transmit the player based data 14 to the computing unit 13 and the equipment module 12 may transmit the equipment based data 16 to the computing unit 13.

The player based data 14 may comprise one or more data formats that may represent the player's activity profile. For example, the player based data 14 may comprise raw measurement data **14*a* that may be provided by a sensor device 17, and/or one or more features 14*b* which may be extracted from the raw measurement data 14*a*, and/or one or more physical player events which may be classified/estimated from the extracted features 14*b* and/or the player's activity profile 14*c* itself which may comprise one or more physical player events. Generally, the activity profile of the player 11' may be represented by the player based data 14** that may comprise different data formats.

The equipment based data 16 may comprise one or more data formats that may represent the motion profile of the equipment. For example, the equipment based data 16 may comprise raw measurement data **16*a* that may be provided by a sensor device 19, and/or one or more features 16*b* which may be extracted from the raw measurement data 16*a*, and/or one or more physical equipment events which may be classified/estimated from the extracted features 16*b* and/or the motion profile 16*c* itself which may comprise one or more physical equipment events. Generally, the motion profile of the equipment 12' may be represented by the equipment based data 16** that may comprise different data formats.

Further details as to the player based data 14 representing the activity profile **14*c* of the player 11' and the equipment based data 16 representing the motion profile 16*c* of the equipment 12' will be described later on with reference to FIG. 6**.

The computing unit 13 may be configured to determine, based on the activity profile **14*c* of the player 11' and on the motion profile 16*c* of the equipment 12', one of a plurality of game scenarios 18 involving the player 11' and the equipment 12'**.

As mentioned above, the player module 11 may comprise a sensor device 17. Since the sensor device 17 may be attached, advantageously in connection with the player module 11, to the player 11', the sensor device 17 may also be referred to as a player sensor device (PSD).

Thus, according to an exemplary embodiment, the player module 11 may comprise a player sensor device 17. The player sensor device 17 may be configured to provide raw measurement data **14*a* that is related with the player 11' to which the player module 11** is attached.

According to an exemplary embodiment, the player sensor device 17 may comprise at least one of a multi-axis accelerometer, an angular rate sensor, a magnetometer and a pressure sensor, the multi-axis accelerometer being configured to provide raw measurement data representing an acceleration of a body part of the player 11' to which the player module 11 is attached, the angular rate sensor being configured to provide raw measurement data representing a rotation of a body part of the player 11' to which the player module 11 is attached, the magnetometer being configured to provide raw measurement data representing a current value of the earth's magnetic field, and the pressure sensor being configured to provide raw measurement data representing a pressure exerted by or at a body part of the player 11' to which the player module 11 is attached.

The player module 11 may be configured to transmit the raw measurement data **14*a* of the player sensor device 17 as the player based data 14 to the computing unit 13, and the computing unit 13 may be configured to determine the activity profile 14*c* of the player 11' from the received raw measurement data 14*a***.

Additionally or alternatively, the player module 11 itself may be configured to determine the activity profile **14*c* of the player 11' from the raw measurement data 14*a*, and the player module 11 may be configured to transmit the activity profile 14*c* of the player 11' as the player based data 14 to the computing unit 13**.

According to a further exemplary embodiment, the player module 11 comprising the above mentioned sensor device 17 may be configured to perform a feature extraction of the raw measurement data **14*a* for estimating/classifying, based on one or more extracted features 14*b*, one or more physical player events which may be executed by the player 11. For example, one or more features 14*b* may be extracted from the raw measurement data 14*a* which features 14*b* may be classified, for example by a feature or a pattern classifier. According to this embodiment, the extracted features 14*b* may be classified into one or more physical player events that may be executed by the respective player 11' to which the player module 11** is attached. A physical player event may, for example, be kicking, running, sprinting, dribbling, and the like.

The player module 11 may be configured to determine the activity profile **14*c* of the player 11' from the extracted one or more features 14*b* and/or from the determined one or more physical player events, and the player module 11 may further be configured to transmit the activity profile 14*c* as the player based data 14 to the computing unit 13. That is, the activity profile 14*c* may be determined in the player module 11**.

Additionally or alternatively, the activity profile **14*c* may be determined in the computing unit 13. Therefore, the player module 11 may, for instance, be configured to transmit the extracted one or more features 14***b* and/or the determined one or more physical player events to the computing unit 13 which may then determine the activity profile 14*c* of the player 11 from the received one or more features 14*b* and/or the received one or more physical player events.

As mentioned above, also the equipment module 12 may comprise a sensor device 19. Since the sensor device 19 may be attached, advantageously in connection with the equipment module 12, to the equipment 12', the sensor device 19 may also be referred to as an equipment sensor device (ESD).

Thus, according to an exemplary embodiment, the equipment module 12 may comprise an equipment sensor device 19 configured to provide raw measurement data 16*a* in connection with the equipment 12' to which the equipment module 12 is attached.

According to an exemplary embodiment, the equipment sensor device 19 may comprise at least one of a multi-axis accelerometer, an angular rate sensor, a magnetometer and a pressure sensor, the multi-axis accelerometer being configured to provide raw measurement data 16*a* representing an acceleration of the equipment 12' to which the equipment module 12 is attached, the angular rate sensor being configured to provide raw measurement data 16*a* representing a rotation of the equipment 12' to which the equipment module 12 is attached, the magnetometer being configured to provide raw measurement data 16*a* representing a current value of the earth's magnetic field, and the pressure sensor being configured to provide raw measurement data 16*a* representing a pressure exerted at the equipment 12' to which the equipment module 12 is attached.

The equipment module 12 may be configured to transmit the raw measurement data 16*a* of the equipment sensor device 19 as the equipment based data 16 to the computing unit 13, and the computing unit 13 may be configured to determine the motion profile 16*c* of the equipment 12' from the received raw measurement data 16*a*.

Additionally or alternatively, the equipment module 12 itself may be configured to determine the motion profile 16*c* of the equipment 12' from the raw measurement data 16*a*, and the equipment module 12 may be configured to transmit the motion profile 16*c* of the equipment 12' as the equipment based data 16 to the computing unit 13.

According to a further exemplary embodiment, the equipment module 12 comprising the above mentioned equipment sensor device 19 may be configured to perform a feature extraction of the raw measurement data 16*a* for classifying, based on one or more extracted features 16*b*, one or more physical events that may be executed by or exerted on the equipment 12'. For example, one or more features 16*b* may be extracted from the raw measurement data 16*a* which features 16*b* may be classified, for example by a feature or a pattern classifier. According to this embodiment, the extracted features 16*b* may be classified into one or more physical equipment events that may be executed by or exerted on the respective equipment 12' to which the equipment module 12 is attached. A physical equipment event may, for example, be being kicked, rolling on the ground, flying through the air, bouncing onto the ground, and the like.

The equipment module 12 may be configured to determine the motion profile 16*c* of the equipment 12 from the extracted one or more features 16*b* and/or from the determined one or more physical equipment events, and the equipment module 12 may further be configured to transmit the determined motion profile 16*c* as the equipment based data 16 to the computing unit 13. That is, the motion profile 16*c* may be determined in the equipment module 12.

Additionally or alternatively, the motion profile 16*c* may be determined in the computing unit 13. Therefore, the equipment module 12 may be configured to transmit the extracted one or more features 16*b* and/or the determined one or more physical equipment events to the computing unit 13 which may then determine the motion profile 16*c* of the equipment 12' from the received one or more features 16*b* and/or the received one or more physical equipment events When the computing unit 13 may have received the player based data 14 and the equipment based data 16 in at least one of the data formats mentioned above, the computing unit 13 may determine, based on the received player based data 14 and on the received equipment based data 16, one out of a plurality of game scenarios 18 in which the player 11' and the equipment 12' are involved.

For example, a soccer player 11' may run over the playing field and may kick a ball 12'. The ball 12' may fly through the air and bounce onto the ground in reaction to the player's kick. The inventive system 10 may be configured to create an activity profile of the player 11' comprising one or more physical payer events indicating that the player 11' ran and kicked the ball. Furthermore, the inventive system 10 may be configured to create a motion profile of the ball 12' comprising one or more physical equipment events indicating that the ball was kicked, flew through the air and bounced onto the ground in reaction to the player's kick.

By fusing the activity profile of the player 11' with the motion profile of the ball 12', the inventive system 10 may determine a certain game scenario. In this example, the system 10 may determine that a certain player 11' played a high pass. If, for instance, more than one player may be comprised by the system 10, a first game scenario may be determined indicating that a first player may have played the high pass to a certain second player, and a second game scenario may be determined indicating that the high pass may have been successfully or unsuccessfully accepted by the second player.

Generally speaking, a game scenario 18 may be a game-specific event in which at least one player 11' and at least one equipment 12' may be involved. A game scenario 18 may be determined by means of an activity profile 14*c* of the at least one player 11' and a motion profile 16*c* of the at least one equipment 12'.

The activity profile 14*c* of the player 11' may be determined in the player module 11 and/or in the computing unit 13. The motion profile 16*c* of the equipment 12' may be determined in the equipment module 12 and/or in the computing unit 13.

An activity profile 14*c* of a player 11' may comprise at least one activity that may be executed by said player 11'. Said activity may also be referred to as a physical player event related with said player 11', such as for example a "kick" executed by said player 11'.

A motion profile 16*c* of an equipment 12' may comprise at least one motion of said equipment 12'. Said motion may also be referred to as a physical equipment event related with said equipment 12'. For example an abrupt decrease in rotation of a ball 12' after having been kicked may be interpreted as the ball 12' "being stopped" by a player.

By fusing the motion profile 16*c* of the equipment 12' with the activity profile 14*c* of the player 11', the computing unit 13 may determine the respective game scenario 18. In the above example, the computing unit 13 may determine a game scenario 18 "high pass" played between a first player and a second player.

Any determined game scenarios 18 may further be analyzed by the inventive system 10. For example, game relevant statistics may be derived from the determined game scenarios 18, e.g. how many high passes and/or low passes were played by a certain player during a match or a training session and optionally with what success rate, how many duels were won or lost by a certain player, and many more. Further examples will follow later on in the description.

Figure 2:
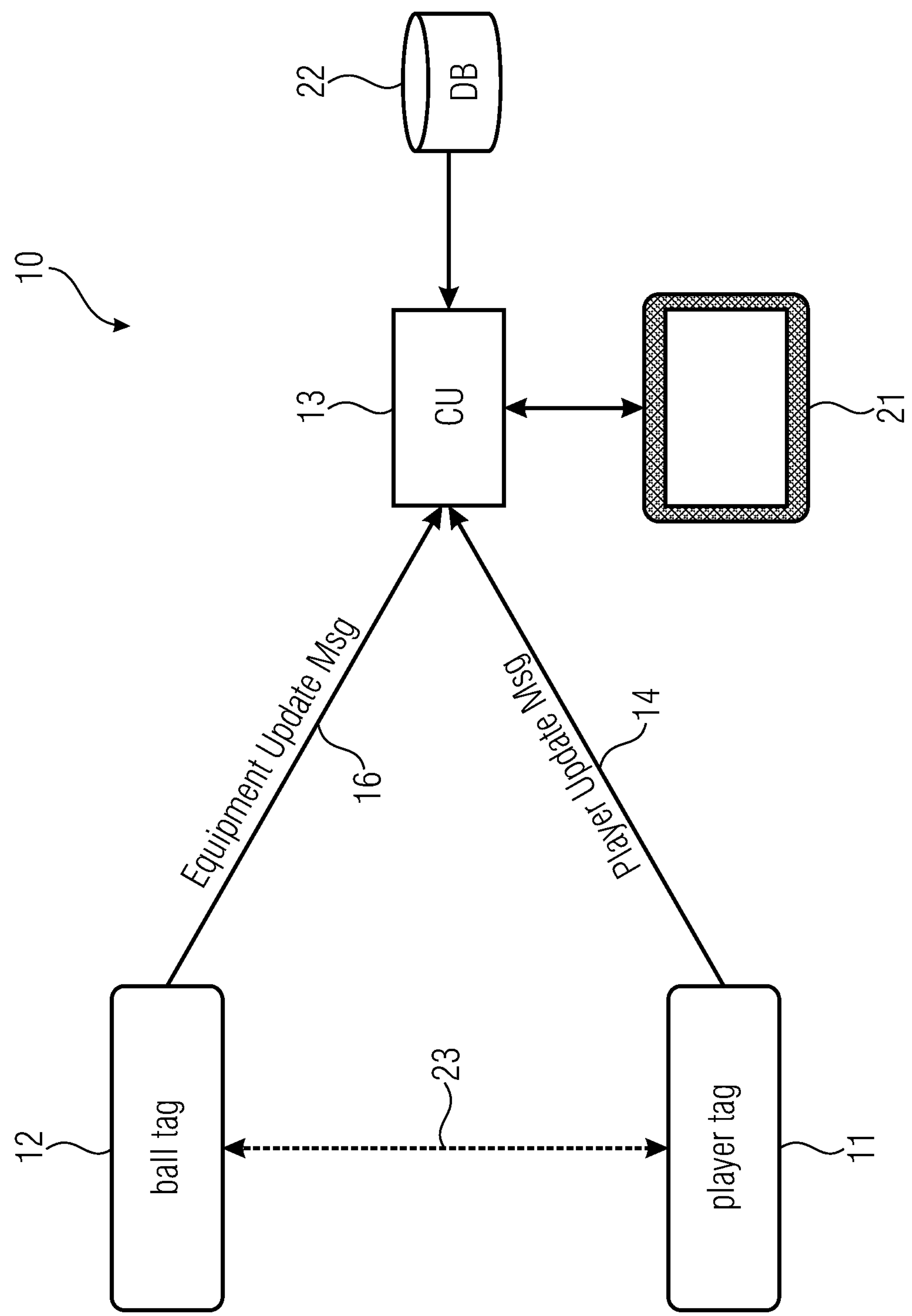
FIG. 2 shows a schematic overview of an example of a communication infrastructure of an inventive system according to an embodiment.

FIG. 2 shows a further overview of an exemplary information sharing architecture that may be deployed in the present inventive concept. The system 10 may comprise a player tag as an example of a player module 11 attached to a player 11', and a ball tag as an example of an equipment module 12 attached to a ball 12'.

The player tag 11 may transmit the player based data 14 to the computing unit 13 in one of several ways and data formats as explained above. In this exemplary embodiment, the player based data 14 may also be referred to as a Player Update Message.

The ball tag 12 may transmit the equipment based data 16 to the computing unit 13 in one of several ways and data formats as explained above. In this exemplary embodiment, the equipment based data 16 may also be referred to as an Equipment Update Message.

The computing unit 13 may comprise, or may be connected with, a graphical user interface (GUI). For example, the GUI may be implemented in a device 21, which may be a stationary or advantageously a handheld device such as a smartphone, a tablet, a notebook or the like. The computing unit 13 may establish a unidirectional or bidirectional communication with the GUI-device 21. For example, the GUI-device 21 may display the game scenario 18 that has been determined by the computing device 13. Additionally or alternatively, the GUI-device 21 may display one or more of the Update Messages, e.g. the player based data 14 or the equipment based data 16. The player based data 14 may be displayed as raw data 14*a*, and/or as one or more extracted features 14*b* and/or as one or more classified physical player events, and/or as an activity profile 14*c* of the player 11'. The equipment based data 16 may be displayed as raw data 16*a*, and/or as one or more extracted features 16*b* and/or as one or more classified physical equipment events, and/or as a motion profile 16*c* of the equipment 12'.

The computing unit 13 may further be connected to a database 22. The database 22 may be an internal database being implemented in the computing unit 13. Additionally or alternatively, the database 22 may be an external database to which the computing unit 13 may be connected via a corresponding interface. For instance, the external database 22 may be connectable via local or remote networks, in particular via the internet.

The database 22 may, for example, comprise additional information for determining the activity profile 14*c* of a certain player 11' and/or the motion profile 16*c* of a sports equipment 12'. The database 22 may, for example, comprise additional information for the classification of physical equipment/player events by means of extracted features 14*b*, 16*b* from the measured raw sensor data 14*a*, 16*a* and other information, like decision domains.

Said additional information may comprise—but may not be limited to:

- information about the player to which the player module is attached,
- information about the sports equipment to which the equipment module is attached,
- information about the player's position in the team formation,
- a previous player based data collected earlier during a match and/or during a training session of the sports game,
- a previous player based data collected earlier during a previous match and/or during a previous training session of the sports game,
- a previous equipment based data collected earlier during a match and/or during a training session of the sports game,
- a previous equipment based data collected earlier during a previous match and/or during a previous training session of the sports game,
- a previous game scenario determined earlier during a match and/or during a training session of the sports game, Said additional information from the database 22 may be used to generate higher level information. For example, the database 22 may comprise information about the playing positions of players 11' (e.g. goal keeper, defense, offense, etc.), physical statistics, habits, event history of game or up to all classified earlier events, or of the progress of the team.

Higher level information may, e.g. be a pass played from a first player A to a second player B, un-/successful pass, time of ball possession, first touch precision, un-/successful interception, won/lost duel, and statistics and analysis based on these higher level information.

More generally, the database 22 may be configured to store additional information about at least one of the player 11', the equipment 12', and a temporal history of the game, and the computing unit 13 may be configured to retrieve said additional information from said database 22 and to determine, based on the activity profile 14*c* of the player 11' and on the motion profile 16*c* of the equipment 12' and on the additional information retrieved from the database 22, the one of a plurality of game scenarios 18 involving the player 11' and the equipment 12'.

As can further be seen in FIG. 2, the player tag 11 and the ball tag 12 may communicate with each other, as indicated by the arrow 23. Thus, the player tag 11 and the ball tag 12 may exchange data with each other, e.g. player based data 14 and/or equipment based data 16. Additionally or alternatively, the player tag 11 and the ball tag 12 may measure and communicate Received Signal Strength—RSSI—values between each other, which will be explained in more detail somewhat later in this description.

Figure 3:
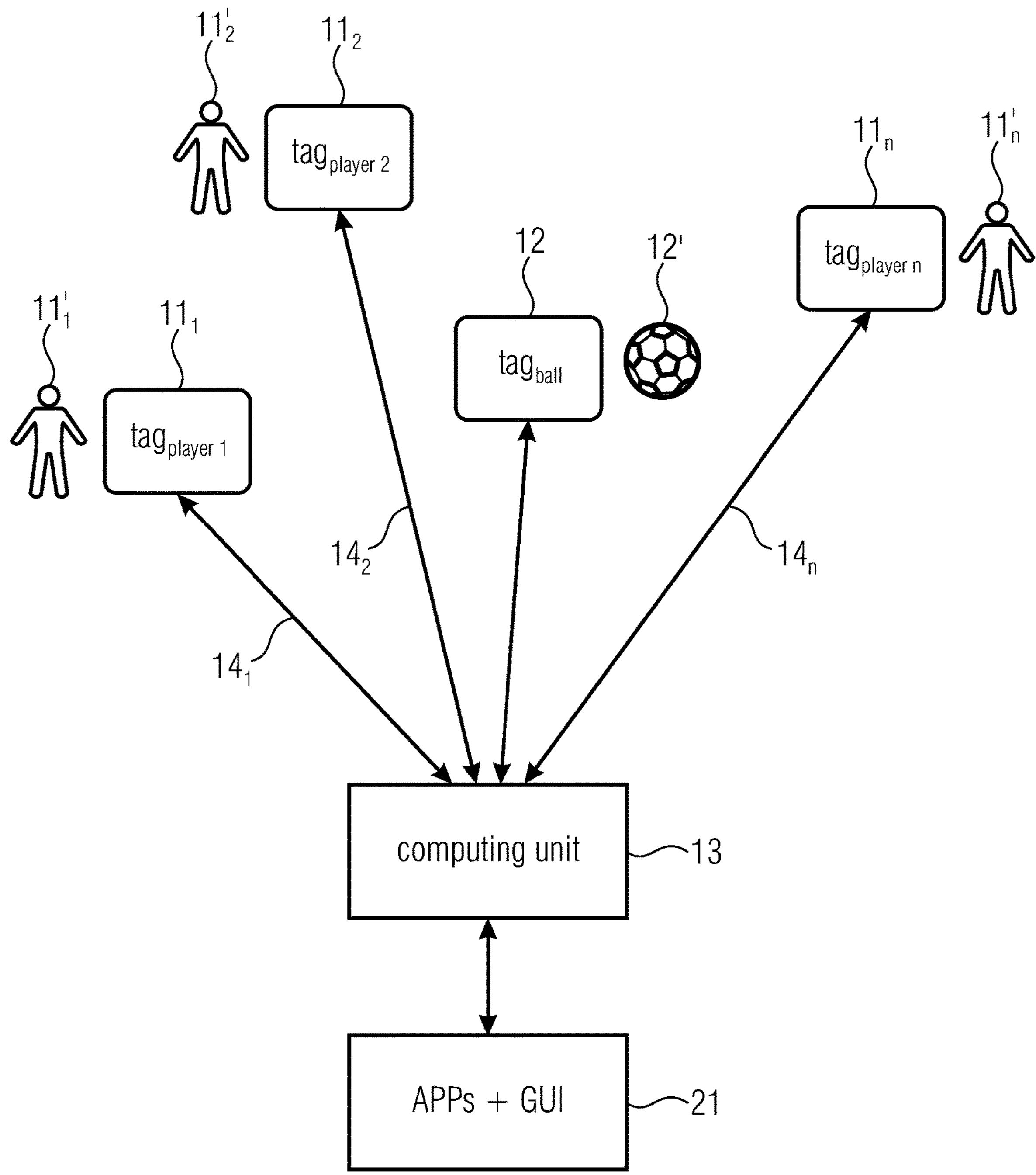
FIG. 3 shows a schematic overview of an inventive system according to a further embodiment.

FIG. 3 shows a schematic overview of an exemplary embodiment of a system 10 comprising more than one player module, e.g. 1, 2, 3, . . . , n player modules. In this example, the system 10 may comprise a first player tag $\mathbf{11}_1$ attached to a first player $\mathbf{11'}_1$, a second player tag $\mathbf{11}_2$ attached to a second player $\mathbf{11'}_2$, an $n^{th}$ player tag $\mathbf{11}_n$ attached to an $n^{th}$ player $\mathbf{11'}_n$, and a ball tag 12 attached to a ball 12'. The system 10 may also comprise more than one equipment module 12, e.g. 1, 2, 3, . . . , n equipment modules.

The first player tag $\mathbf{11}_1$ may transmit first player based data $\mathbf{14}_1$ to the computing unit 13, the second player tag $\mathbf{11}_2$ may transmit second player based data $\mathbf{14}_2$ to the computing unit 13, and the $n^{th}$ player tag $\mathbf{11}_n$ may transmit $n^{th}$ player based data $\mathbf{14}_n$ to the computing unit 13.

Thus, according to an exemplary embodiment, the system 10 may comprise a further (e.g. a second) player module $\mathbf{11}_2$ being attachable to a further player $\mathbf{11'}_2$, wherein the computing unit 13 may be configured to receive further player based data $\mathbf{14}_2$ from the further player module $\mathbf{11}_2$, the further player based data $\mathbf{14}_2$ representing a further activity profile of the further player $\mathbf{11'}_2$.

The computing unit 13 may be configured to determine, based on the activity profile 14*c* of the first player $\mathbf{11'}_1$ and on the further activity profile of the further player $\mathbf{11'}_2$ and on the motion profile 16*c* of the equipment 12', one of a plurality of game scenarios 18 involving the player $\mathbf{11'}_1$ and the further player $\mathbf{11'}_2$ and the equipment 12'.

For example, a ball 12' may be passed from the first player $\mathbf{11'}_1$ to the second player $\mathbf{11'}_2$. The first player $\mathbf{11'}_1$ may play a low pass, for example. The activity profile 14*c* of the first player $\mathbf{11'}_1$ may indicate (e.g. by means of extracted features 14*b* or classified physical player events) that the first player $\mathbf{11'}_1$ kicked the ball 12', the motion profile 16*c* of the ball 12' may indicate (e.g. by means of extracted features 16*b* or classified physical equipment events) that the ball 12' has been kicked and is rolling on the ground, and the further activity profile of the second player $\mathbf{11'}_2$ may indicate (e.g. by means of extracted features $\mathbf{14}_2b$ or classified physical player events) that the second player $\mathbf{11'}_2$ stopped the ball 12'.

Then the computing unit 13 may be configured to fuse the activity profile 14*c* of the first player $\mathbf{11'}_1$ with the further activity profile of the further player $\mathbf{11'}_2$ and the motion profile 16*c* of the equipment 12' for determining one of a plurality of game scenarios 18 involving the first player $\mathbf{11'}_1$, the second player $\mathbf{11'}_2$ and the equipment 12'. In this example, the determined game scenario 18 may be a successful low pass played from the first player $\mathbf{11}_1$ to the second player $\mathbf{11}_2$.

According to a further exemplary embodiment, the system 10 may be configured to temporally synchronize player based data 14 with equipment based data 16. For example, a motion profile 12 of an equipment 12' may be temporally synchronized with an activity profile 14 of a player 11'. For example, a physical player event (e.g. kick) may be temporally associated with a physical equipment event (e.g. having been kicked).

For example, the player module 11 may be configured to generate the player based data 14 during a predetermined time window, and also the equipment module 12 may be configured to generate the equipment based data 16 during a predetermined time window. The computing unit 13 may receive the player based data 14 and the equipment based data 16, and the computing unit 13 may further be configured to timely synchronize the received player based data 14 and the received equipment based data 16 such that the time windows of the player based data 14 and the equipment based data 16 at least partially overlap in the time domain.

For example, the player module 11 may collect one or more player based data 14 during a first time window between $t_1$ and $t_2$. Said first time window may comprise a temporal length between a few milliseconds and a few seconds. A shorter time window may provide a higher accuracy of the real-time capability of the system 10. For example, temporal windows in the range of milliseconds may provide a very good real time experience to the user. The temporal length of the above mentioned first time window may range between 0.05 s and 2.00 s, or between 0.25 s and 1.00 s, or between 0.40 s and 0.75 s. In some examples, the temporal length of the first time window may be about 0.50 seconds. During this first time window the player 11' may have kicked the ball 12' which may be representable in the activity profile 14*c*.

The equipment module 12 may collect one or more equipment based data 16 during a second time window between $t_3$ and $t_4$, wherein $t_3$ may be positioned between $t_1$ and $t_2$ so that the first and the second time windows at least partially overlap in the time domain. The temporal length of the above mentioned second time window may range between 0.05 s and 2.00 s, or between 0.25 s and 1.00 s, or between 0.40 s and 0.75 s. In some examples, the temporal length of the second time window may be about 0.50 seconds. The player based data 14 and the equipment based data 16 may be temporally synchronized in at least the partially overlapping area.

Preferably, the temporal window of the equipment based data 16 and the temporal window of the player based data 14 may comprise the same window size and may comprise a congruent overlapping area in the time domain. For example, $t_1=t_3$ and $t_2=t_4$.

The player based data 14 may comprise one or more player features 14*b* that may be extracted from raw sensor measurement data 14*a* of the sensor device 17 comprised by the player module 11. Accordingly, said one or more player features 14*b* may, for instance, be extracted by using a temporal windowing scheme as explained above with reference to the player based data 14 in general. For example, the player module 11 may extract one or more player features 14*b* from the raw measurement data 14*a* during a first time window of, e.g. between $t_1$ and $t_2$.

The equipment based data 16 may comprise one or more equipment features 16*b* that may be extracted from raw sensor measurement data 16*a* of the sensor device 19 comprised by the equipment module 12. Accordingly, said one or more equipment features 16*b* may, for instance, be extracted by using a temporal windowing scheme as explained above with reference to the equipment based data 16 in general. For example, the equipment module 12 may extract one or more equipment features 16*b* from the raw measurement data 16*a* during a second time window, e.g. between $t_3$ and $t_4$.

By means of the above described temporal synchronization of the player based data 14 with the equipment based data 16, a temporal association between a motion profile 16*c* of the equipment 12' and an activity profile 14*c* of the player 11' may be provided. For example, a physical player event may be associated with a physical equipment event which events may have happened at approximately the same time during the match. Thus, a probability of correctly determining a game scenario 18 in which the player 11' and the equipment 12' are involved may be significantly increased.

As already described with reference to FIG. 1, each of the ball tag, i.e. the equipment module 12, and the player tag, i.e. the player module 11, may comprise at least one sensor device 17, 19. The respective sensor devices 17, 19 may comprise various sensors, such as accelerometers, magnetometers, gyroscopes/angular rate sensors, pressure sensors, which sensors may be connected to a processing unit. In a particular embodiment, the player module 11 and/or the equipment module 12 may comprise a sensor device 17, 19 comprising at least a multi-axis accelerometer. The data retrieved from the respective sensor device 17, 19 may be optionally saved in a buffer and may be communicated to the computing unit 13 advantageously via a radio interface.

Figure 4:
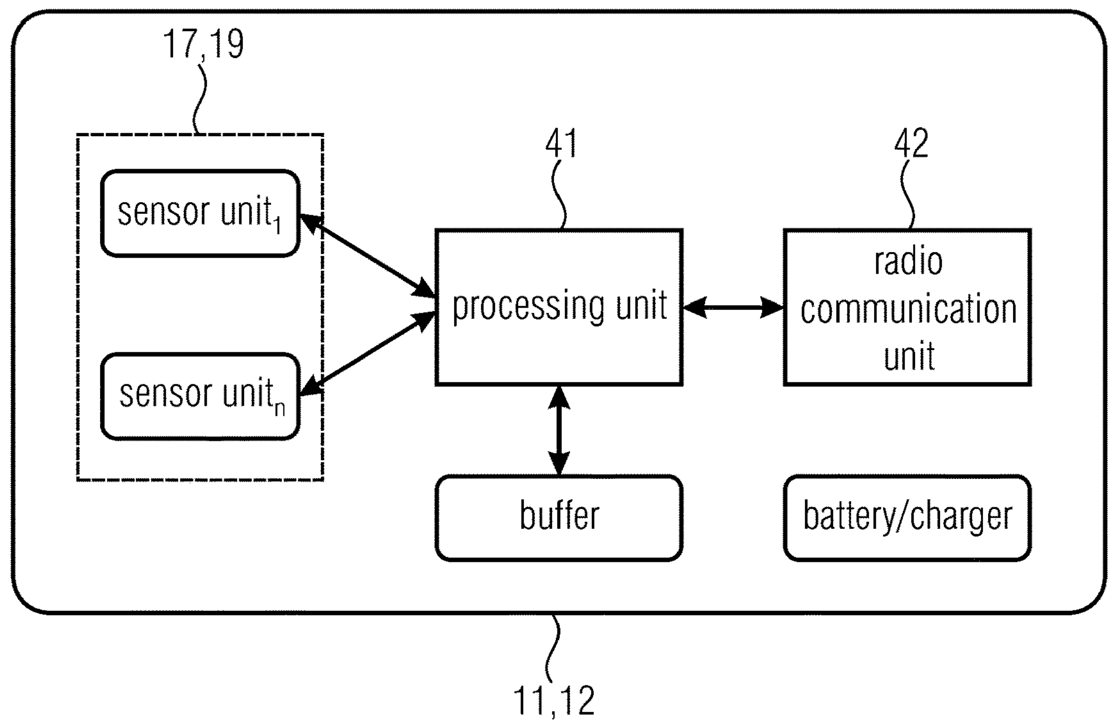
FIG. 4 shows a schematic high-level description of a player module and an equipment module according to an embodiment.

A higher-level functional description of the player module 11 is depicted in FIG. 4, which higher-level functional description may also be respectively valid for an equipment module 12.

An optional processing unit 41 inside the respective module 11, 12 may carry out a signal analysis for extracting relevant features 14$b$, 16$b$ (c.f. FIG. 1) from the raw measurement signals 14$a$, 16$a$ retrieved from the respective sensor device 17, 19. The features 14$b$, 16$b$ extracted by the respective module 11, 12 may include, but are not limited to, spin rate, impact strength and time, statistical moments, motion state of the respective module 11, 12. Accordingly, the activity profile 14$c$ of a player 11' may be determined from these extracted features 14$b$ if the signal 14$a$ stems from the player module 11, or the motion profile 16$c$ of the equipment 12' may be determined from these extracted features 16$b$ if the signal stems from the equipment module 12.

The player based data 14 and the equipment based data 16, respectively, may be transmitted to the computing unit 13 via a radio communication unit 42. The player based data 14 and/or the equipment based data 16 may be transmitted to the computing unit 13 in at least one of the data formats as described above with reference to FIG. 1. For example, the player tag 11 and/or the ball tag 12 may be configured to transmit raw measurement data 14$a$, 16$a$ as the player/equipment based data 14, 16, and/or extracted features 14$b$, 16$b$ as the player/equipment based data 14, 16, and/or classified physical events as the player/equipment based data 14, 16, and/or a the activity/motion profiles 14$c$, 16$c$ themselves as the player/equipment based data 14, 16. Even though raw measurement signals 14$a$, 16$a$ may optionally be transmitted, this may cause a higher data volume to be communicated, e.g. three-axis acceleration data with 300 Hz sampling rate. Thus, processing the raw measurement data 14$a$, 16$a$ already on the respective player/equipment module 11, 12 may be advantageous.

Figure 5:
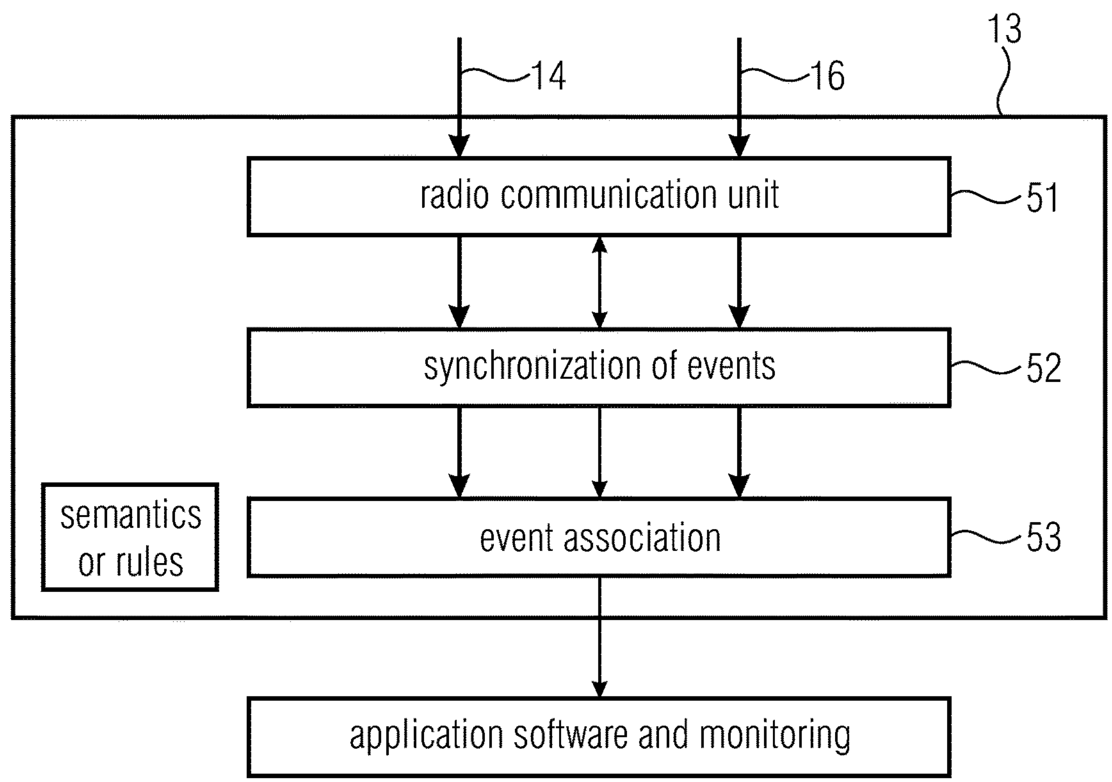
FIG. 5 shows a schematic high-level description of a computing unit according to an embodiment.

FIG. 5 shows a higher-level functional description of the computing unit 13. The computing unit 13 may receive player based data 14 and/or equipment based data 16 from the respective modules 11, 12 via a radio communication unit 51.

The received player based data 14 and/or equipment based data 16 may comprise a timestamp and a payload. The payload may comprise at least one of raw signals, extracted features, classified physical events and motion/activity profiles. The received player based data 14 and/or equipment based data 16 may be temporally synchronized between different modules 11, 12 in a synchronizing stage 52. In the example shown in FIG. 5, physical events may be synchronized in the synchronizing stage 52 as one non-limiting example of player based data 14 and/or equipment based data 16.

The synchronized player based data 14 and/or equipment based data 16 may then be associated to one another in a data association stage 53, e.g. by using semantics or rules. In the example shown in FIG. 5, the previously mentioned physical events may be associated with one another in an event association stage 53.

Figure 6:
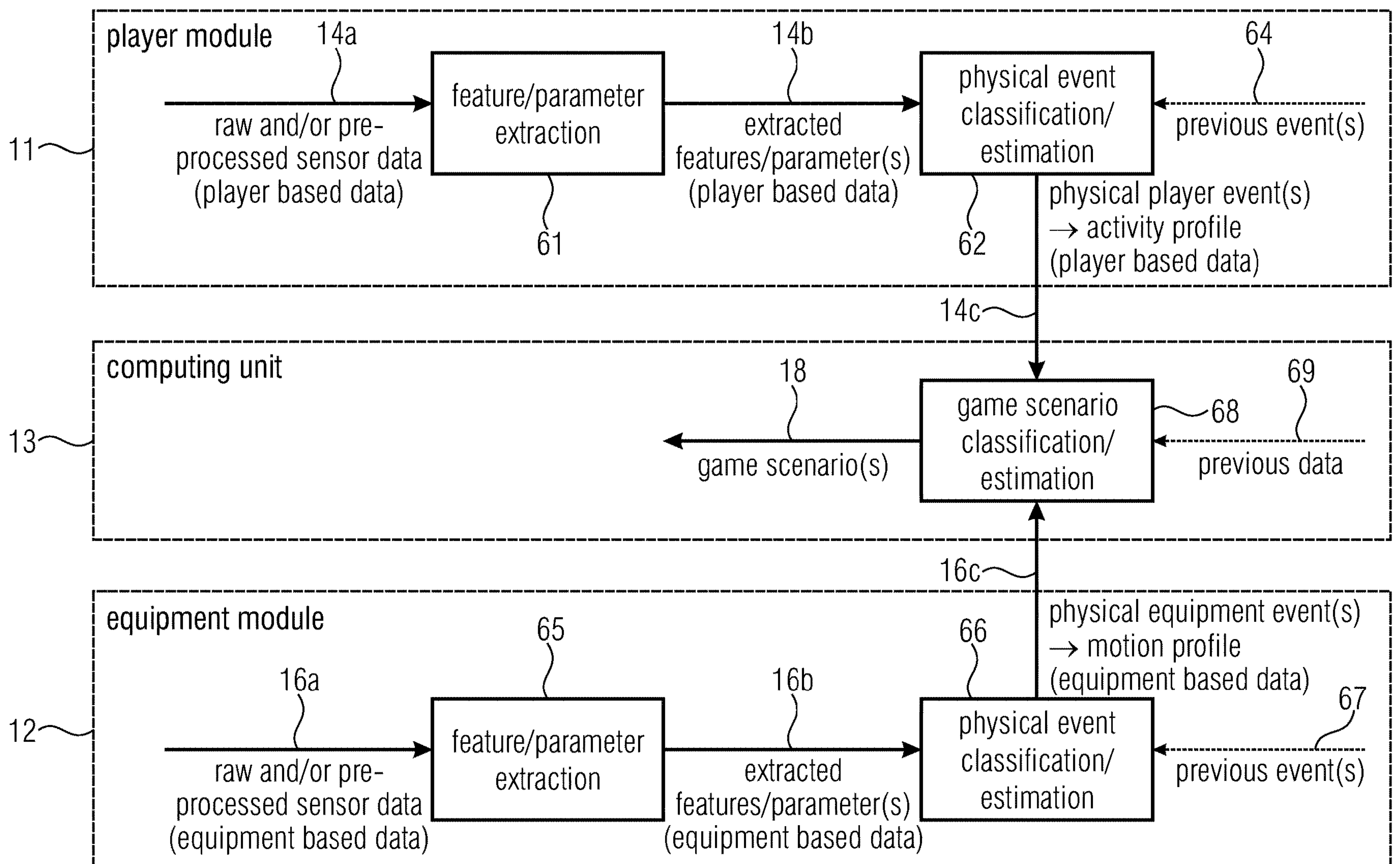
FIG. 6 shows a schematic block diagram of determining an activity profile, a motion profile and a game scenario based thereon, according to an embodiment.

FIG. 6 shows a schematic overview of an example of possible data handling of the inventive system 10 according to an embodiment.

The player module 11 may comprise a feature extraction stage 61, which may also be referred to as a parameter extraction stage. Raw and/or pre-processed sensor measurement data 14$a$ (as one option of player based data 14), which may be generated by the sensor device 17 comprised by the player module 11, may be fed into the feature extraction stage 61. The feature extraction stage 61 may extract one or more features or parameters from the raw and/or pre-processed sensor measurement data 14$a$.

Figure 7:
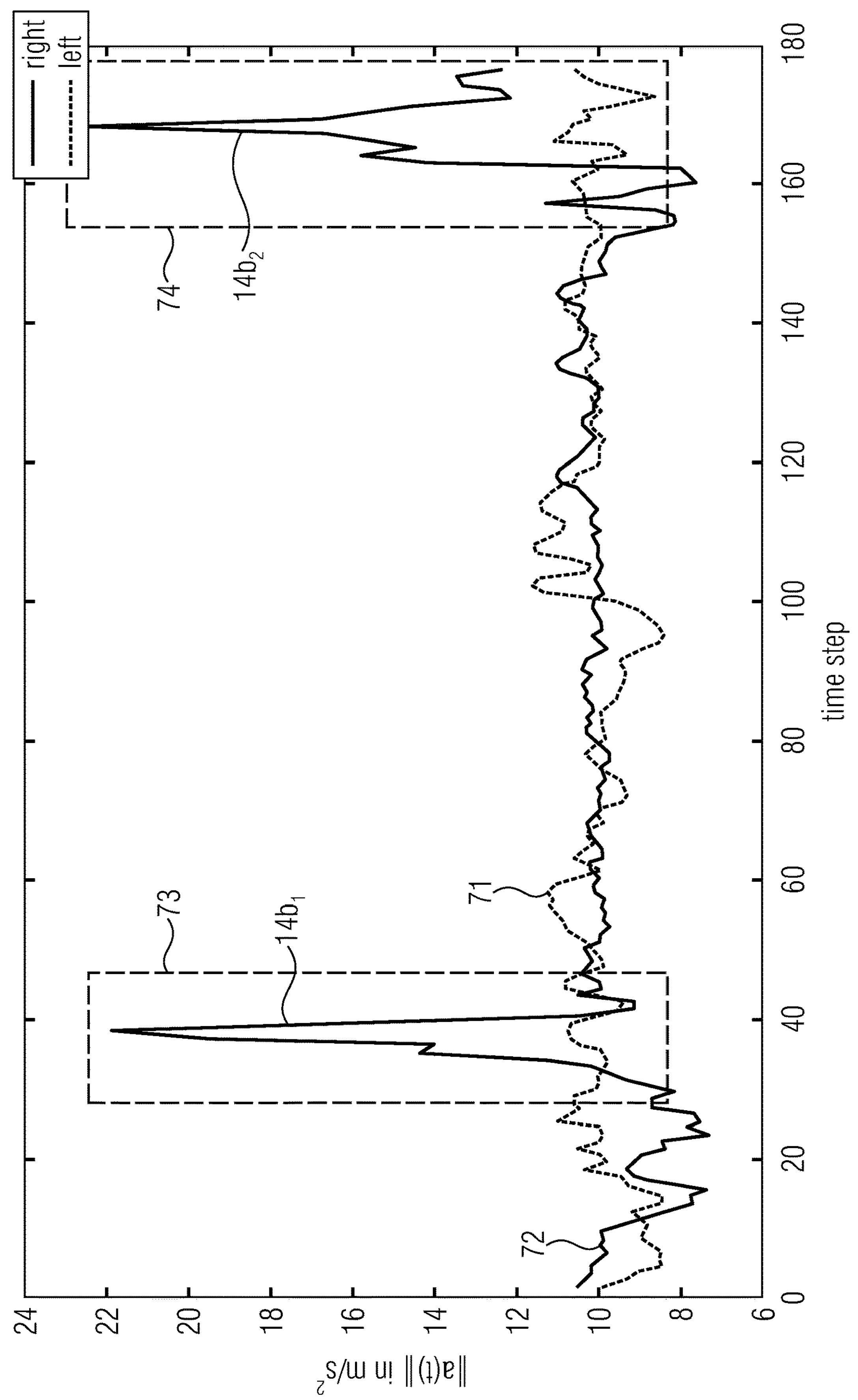
FIG. 7 shows an acceleration measurement diagram representing acceleration values obtained from two player modules attached to one player, according to an embodiment.

As a non-limiting example for a feature extraction it shall briefly be referred to FIG. 7, which shows a diagram comprising raw measurement data that has been obtained by a first and a second player module $\mathbf{11}_1$, $\mathbf{11}_2$ which have both been attached to one player 11'. In particular, the first player module $\mathbf{11}_1$ was attached to the left shin guard of the player 11' and the second player module $\mathbf{11}_2$ was attached to the right shin guard of the player 11'.

Each of the player modules $\mathbf{11}_1$, $\mathbf{11}_2$ comprised an accelerometer which delivered raw measurement data. The accelerometer data that is depicted in the above discussed FIG. 7 represents the respective norm of the respective accelerometer-vector. In particular, the first graph 71 shows the data of the first player module $\mathbf{11}_1$ attached to the left shin guard. The second graph 72 shows the data of the second player module $\mathbf{11}_2$ attached to the right shin guard.

More particularly, the diagram shows the temporal behavior of the norm of the acceleration vector obtained from the accelerometer on the left leg 71 and the right leg 72 of the player 11'. The relevant information is contained in the time instances where the norm apparently deviates from the force of gravity at ~9.81 m/s$^2$. Parameters or features, exemplarily represented by a timely limited increase in the norm of the acceleration vector of the second player module $\mathbf{11}_2$, may be detected as highlighted in the rectangular boxes 73, 74.

These two features (or parameters) may be detected in the aforementioned feature extraction stage 61 (c.f. FIG. 6). Accordingly, the two peaks in the diagram may be referred to as features, in particular as player features $\mathbf{14}b_1$, $\mathbf{14}b_2$.

According to an example, at least one of the extracted features $\mathbf{14}b_1$, $\mathbf{14}b_2$ may be transmitted to the computing unit 13 as the player based data 14, wherein the computing unit 13 may determine the activity profile of the player 11' from the received extracted features $\mathbf{14}b_1$, $\mathbf{14}b_2$.

Additionally or alternatively, as shown in the example of FIG. 6, the activity profile of the player 11' may be determined by the player module 11. For example, the extracted features $\mathbf{14}b_1$, $\mathbf{14}b_2$ may be fed into a physical event classification/estimation stage 62. In said physical event classification/estimation stage 62 at least one of the extracted features $\mathbf{14}b_1$, $\mathbf{14}b_2$ may be classified as a physical event. Physical events of the player module 11 may also be referred to as physical player events.

With reference to FIG. 7 again, the depicted part of the measurement shows a temporal section of a scenario where passes were played between two players. Each of the above mentioned two player features $\mathbf{14}b_1$, $\mathbf{14}b_2$ highlighted in the rectangular boxes 73, 74 may represent a kick that has been executed by one of the players 11' to which the first and second player modules $\mathbf{11}_1$, $\mathbf{11}_2$ were attached. Thus, the event classification/estimation stage 62 (c.f. FIG. 6) may estimate or classify each one of these two features $\mathbf{14}b_1$, $\mathbf{14}b_2$ as a physical event "kick". It may be visible, and even be classifiable, that the ball was kicked with the right leg.

Referring back to FIG. 6, the physical event classification/estimation stage 62 may determine the activity profile 14$c$ of the player 11' from the at least one classified physical player event. In other words, the activity profile 14$c$ of the player 11' may comprise at least one physical player event. An activity profile 14$c$ of the player 11' may comprise a plurality of physical player events in a consecutive temporal order, e.g. running, then sprinting, then kicking, and so on. In this exemplary embodiment, the activity profile 14$c$ of the player 11' may be determined by the player module 11 itself.

Additionally or alternatively, the physical event classification/estimation stage 62 may process one or more previous events 64, which may have already been classified previously, in the step of classifying a feature as a physical player event.

Additionally or alternatively, the classified physical player events may be transmitted to the computing unit 13, as a non-limiting example of player based data 14, wherein the computing unit 13 may generate the activity profile of the player 11' based on the received physical player events.

As can further be seen in FIG. 6, also the equipment module 12 may comprise a feature/parameter extraction stage 65 and a physical event classification/estimation stage 66 both of which having the same or a similar functionality as the above described feature/parameter extraction stage 61 and the physical event classification/estimation stage 62 comprised by the player module 11.

For example, raw and/or pre-processed sensor data 16*a*, which may be generated by the sensor device 19 comprised by the equipment module 12, may be received by the feature/parameter extraction stage 65. One or more equipment features may be extracted from the signal, as exemplarily explained above with reference to the player module 11.

Additionally or alternatively, the one or more extracted equipment features 16*b* may be transmitted to the computing unit 13, as a non-limiting example of equipment based data 16, wherein the computing unit 13 may determine a motion profile of the equipment 12' from the received one or more equipment features 16*b*.

Additionally or alternatively, as depicted in FIG. 6, the one or more extracted equipment features 16*b* may be fed into the physical event classification/estimation stage 66 in which a classification of the received one or more extracted equipment features 16*b* may take place, as exemplarily explained above with reference to the player features 14*b* and the player module 11.

For example, an equipment feature representing an impact to the ball 12' may be extracted from the signal of the sensor device 19 by the feature/parameter extraction stage 65. Said impact may be classified as a physical equipment event "ball was kicked" by the physical event classification/estimation stage 66. These physical events may also be referred to as physical equipment events, or in this example as physical ball events.

The physical event classification/estimation stage 66 may generate the motion profile 16*c* of the equipment 12' based on the at least one classified physical equipment event. In other words, the motion profile 16*c* of the equipment 12' may comprise at least one physical equipment event. A motion profile 16*c* of the equipment 12' may comprise a plurality of physical equipment events in a consecutive temporal order, e.g. being kicked, then flying through the air, then rolling on the floor. In this exemplary embodiment, the motion profile 16*c* of the equipment 12' may be determined by the equipment module 12 itself.

Additionally or alternatively, the physical event classification/estimation stage 66 may process one or more previous events 67, which may have already been classified previously, in the step of classifying a feature as a physical ball event.

Additionally or alternatively, the one or more classified physical equipment events may be transmitted to the computing unit 13, as a non-limiting example of equipment based data 16, wherein the computing unit 13 may determine the motion profile of the equipment 12' from the received physical equipment events.

In result, the computing unit 13 may receive at least a player based data 14 from the player module 11 and an equipment based data 16 from the equipment module 12.

The player based data 14 may be at least one of raw and/or pre-processed sensor data 14*a*, which may be generated by the sensor device 17 comprised by the player module 11, and/or one or more extracted player features 14*b*, and/or one or more classified physical player events, wherein one or more physical player events may yield an activity profile 14*c* of the player 11'. The equipment based data 16 may be at least one of raw and/or pre-processed sensor data 16*a*, which may be generated by the sensor device 19 comprised by the equipment module 12, and/or one or more extracted equipment features 16*b*, and/or one or more classified physical equipment events, wherein one or more physical equipment events may yield a motion profile 16*c* of the equipment 12'.

Independent of whether the motion profile 16*c* of the equipment 12 and the activity profile 14*c* of the player 11 were determined by the respective equipment/player module 11, 12 or by the computing unit 13, the computing unit 13 may determine a game scenario based on the motion profile 16*c* and the activity profile 14*c*.

As shown in FIG. 6, the computing unit 13 may comprise a Game Scenario Classification/Estimation Stage 68 in which the motion profile 16*c* of the equipment 12' and the activity profile 14*c* of the player 11' may be classified into one out of a plurality of game scenarios 18.

For example, a plurality of game scenarios may be stored in the computing unit 13. The computing unit 13 may compare both the activity profile 14*c* and the motion profile 16*c* with respective reference profiles which may be associated with classes representing typical game scenarios. Accordingly, the received activity profile 14*c* and the motion profile 16*c* may be classified into one class, e.g. into one out of the plurality of game scenarios 18.

Additionally or alternatively, the Game Scenario Classification/Estimation Stage 68 may process one or more previous data (e.g. player based data 14 and/or equipment based data 16) in the step of classifying the activity profile 14*c* and the motion profile 16*c* into a game scenario.

In the following, a brief summary of FIG. 6 shall give some examples how features, physical events and motion or activity profiles may be distinguished:

A feature may, for instance, be a parameter (e.g. a vector) obtained from the raw measurement data of the respective sensor device. Accordingly, a feature may, for example, be an energy of a three-axis accelerometer signal. A set or a sequence of sets of sensor data may be used to obtain features (e.g. energy of the accelerometer signal, spectral features, and the like). Features may be extracted from the sensor data as a pre-processing stage of a classification of said sensor data.

An event may, for instance, be a classification result obtained from the raw measurement data or from other available information, such as the extracted features. On the modules, these events may be physical events of the equipment or the player, respectively (e.g. ball is rolling, player is running).

One abstraction level higher are sport-related events, which may also be referred to as game scenarios (e.g. a pass played between two players). Game scenarios may be determined based on an activity profile of a player and a motion profile of an equipment. An activity profile of a player may comprise at least one physical player event, or a plurality of (consecutive) physical player events. A motion profile of the equipment may comprise at least one physical equipment event, or a plurality of (consecutive) physical equipment events.

A feature or a sequence of features and/or knowledge about the prior situation (features, physical events, sport-related events (including knowledge about all players/equipment)) may be used to classify/estimate a physical event.

A physical event or a sequence of physical events and/or knowledge about the prior situation (physical events, sport-related events (including knowledge about all players/equipment)) may be used to estimate sport-related events, i.e. game scenarios.

As mentioned before, for example with reference to FIG. 3, the inventive system 10 may comprise one or more player modules $\mathbf{11}_1$, $\mathbf{11}_2$. As a non-limiting example, a concept of a collaboration between two player modules $\mathbf{11}_1$, $\mathbf{11}_2$ and one equipment module 12 may be explained by a detection of a typical scenario in a football match whereby a player 'A' passes a ball 12' to another player 'B'. At least one player module $\mathbf{11}_1$ may be attached to player 'A', at least the further player module $\mathbf{11}_2$ may be attached to player 'B' and at least one equipment module 12 may be attached to the ball 12'.

In this example, player 'A' may kick the ball 12' and the ball 12' may fly through the air before it strikes the ground and be stopped by player 'B'. In the inventive system 10 as described herein, the physical player event "kick" from player 'A' may be identified by the player module $\mathbf{11}_1$ attached to player 'A'. Such a physical event may be identified by a variety of techniques, such as matching pattern, frequency analysis and so on. Likewise, the equipment module 12 attached to the ball 12' may also (e.g. simultaneously) identify one or more equipment features such as impacts, rotation rate, and impact frequency, and it may also estimate parameters of flight of the ball 12' such as height, distance of travel, spin and so on. Furthermore, the equipment module 12 may generate physical equipment events from said equipment features. By combining the information from the player module $\mathbf{11}_1$ attached to player 'A' with the equipment module 12 attached to the ball 12', e.g. by using semantics that may associate the sequence of extracted features into an action (e.g. physical player event and activity profile and/or physical equipment event and motion profile), it can be inferred that player 'A' has kicked the ball 12' away from him. At the other end, when the ball 12' is stopped by the second player 'B', the player module 112 attached to player 'B' and the equipment module 12 attached to the ball 12' may identify the respective events and communicate it to the computing unit 13. The computing unit 13 may then synchronize the received physical events (and/or activity profile and/or motion profile) and associate them to infer that the ball 12' was successfully passed from player 'A' to player 'B'.

Figure 8A:
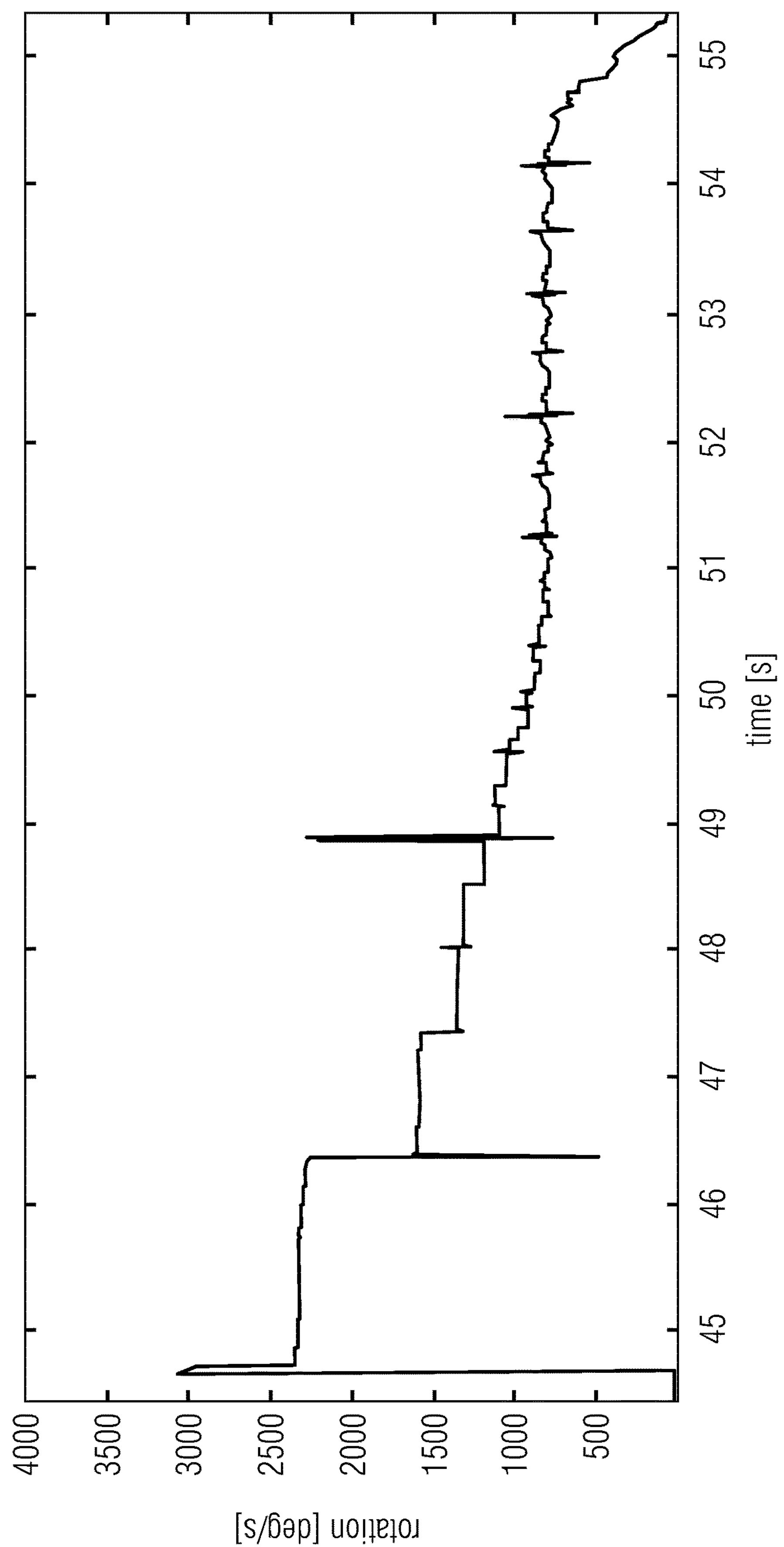
FIG. 8A shows a rotation measurement diagram representing rotation values obtained from an equipment module attached to a ball during a high pass, according to an embodiment.
Figure 8B:
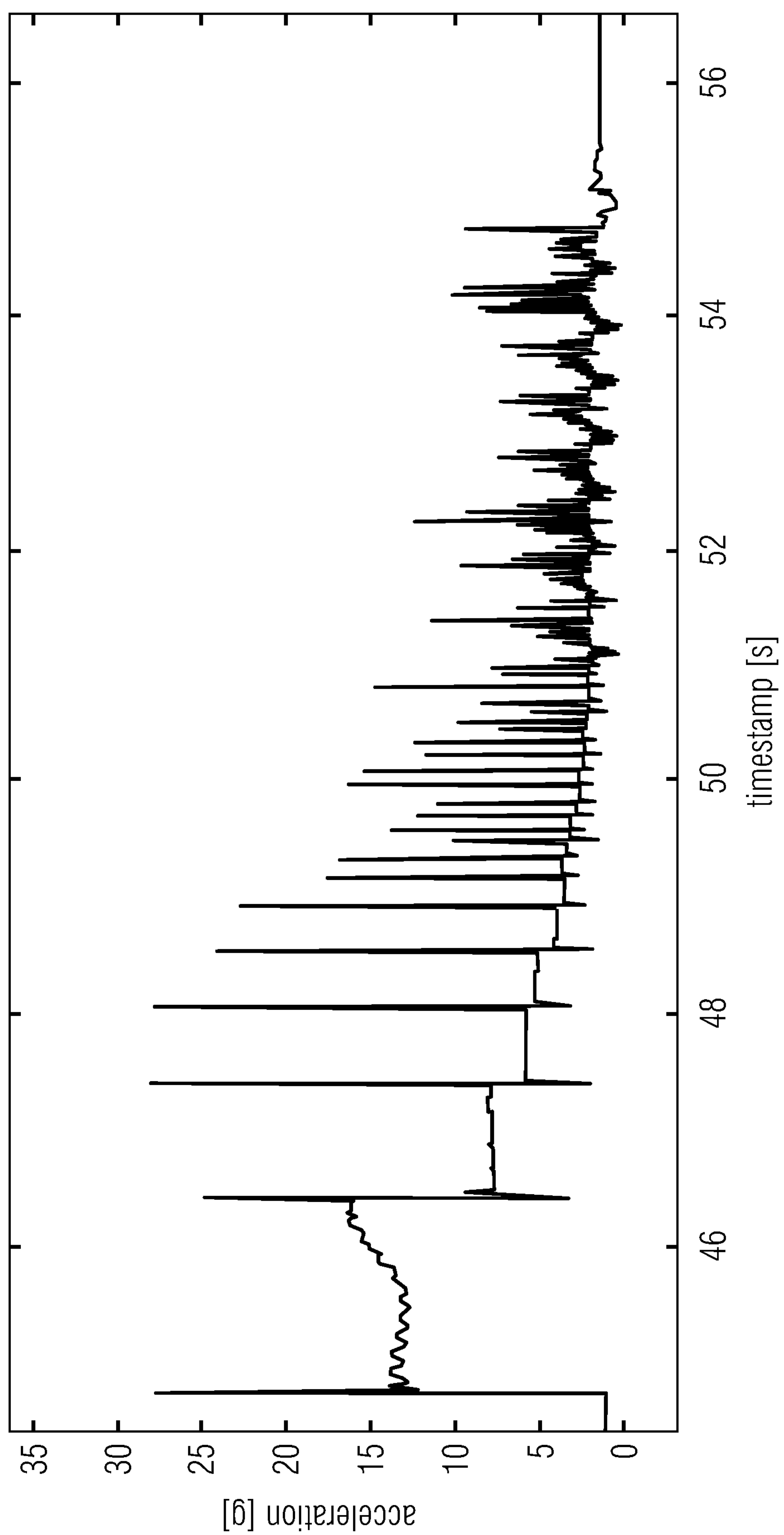
FIG. 8B shows an acceleration measurement diagram representing acceleration values obtained from an equipment module attached to a ball during a high pass, according to an embodiment.
Figure 8C:
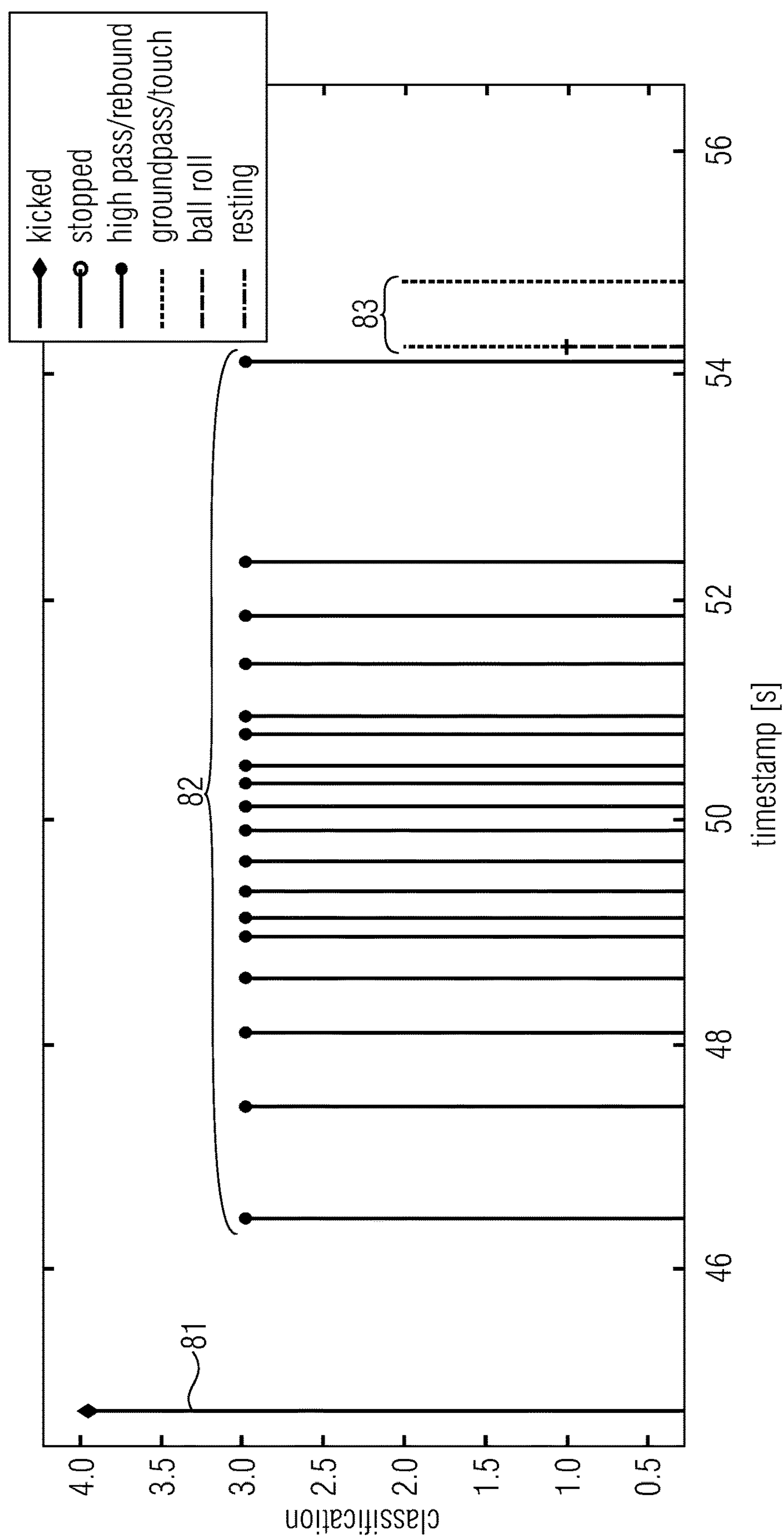
FIG. 8C shows a motion profile of the ball which motion profile was determined from the rotation measurement data and the acceleration measurement data, according to an embodiment.

FIGS. 8A, 8B and 8C show an example of equipment based data which has been collected while a player kicked a ball and played a high pass. An equipment module was attached to the ball, wherein the equipment module comprised a sensor device comprising a rotation sensor and an acceleration sensor.

FIG. 8A shows the raw measurement data of the rotation sensor. FIG. 8B shows the raw measurement data of the acceleration sensor. Features were extracted and classified into physical ball events, as described above. These physical ball events are collected and combined in a motion profile, which is shown in FIG. 8C.

As can be seen at the beginning of the time scale of the rotation diagram in FIG. 8A and of the acceleration diagram in FIG. 8B, a first peak is detectable which can be extracted and classified as a physical ball event 81 (FIG. 8C) "ball was kicked".

With advancing time, the rotation of the ball decreases (FIG. 8A) and the acceleration of the ball (FIG. 8B) comprises temporally consecutive peaks. This may happen when the ball, after having been kicked, flies through the air and then continuously bounces (rebound) on the ground. These peaks can be extracted and classified as physical ball events 82 (FIG. 8C) "high pass/rebound".

The last two physical events 83 shown in FIG. 8 were classified as "Ground Pass/Touch". This may happen when the rebound of the ball only comprises a low height at the end of a high pass. Said low height bouncing may also happen when a low pass is played. Thus, it may be interpreted as a low pass.

However, a plurality of physical ball events may yield a motion profile of the ball as exemplarily depicted in FIG. 8C. This motion profile may indicate that a high pass was played with the ball.

A corresponding activity profile (not shown) of a player that may have kicked the ball may be fused with the motion profile (FIG. 8C) of the ball. Thereby, the computing unit 13 may determine a corresponding game scenario involving the player and the ball, namely that said player may have played the high pass.

A further activity profile of a further player module attached to a further player may be processed by the computing unit 13. This further activity profile may indicate that the further player may have received the pass. Accordingly, the computing unit 13 may determine a corresponding game scenario involving both players and the ball, namely that a certain first player may have played the high pass to a certain second player.

Game relevant statistics may be created from the determined game scenarios. For example, if the second player who received the high pass was a member of the same team, then this would have been a successful high pass. If the second player was instead a member of the other team, then this would have been an unsuccessful high pass.

Figure 9A:
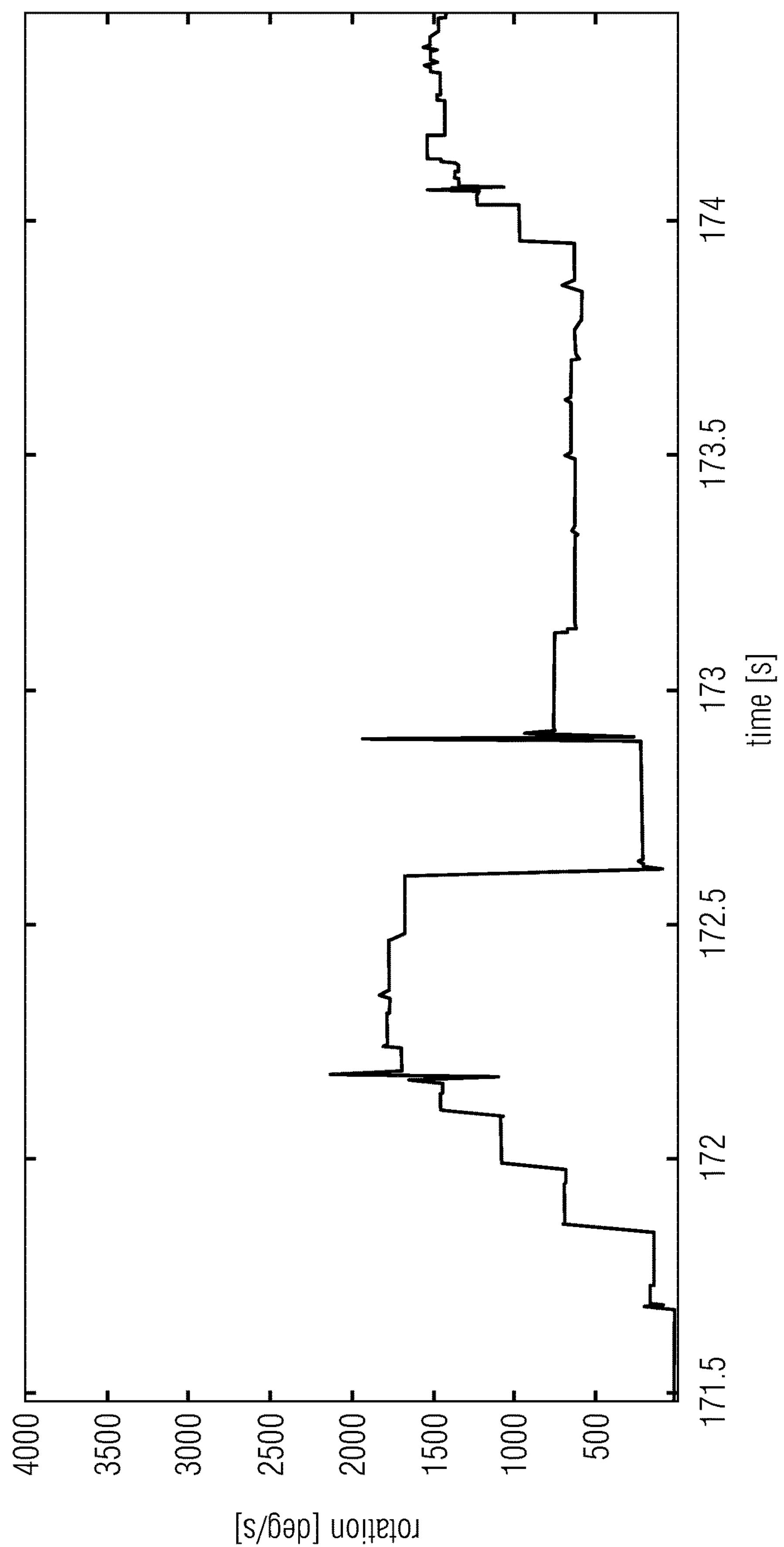
FIG. 9A shows a rotation measurement diagram representing rotation values obtained from an equipment module attached to a ball during a low/ground pass, according to an embodiment.
Figure 9B:
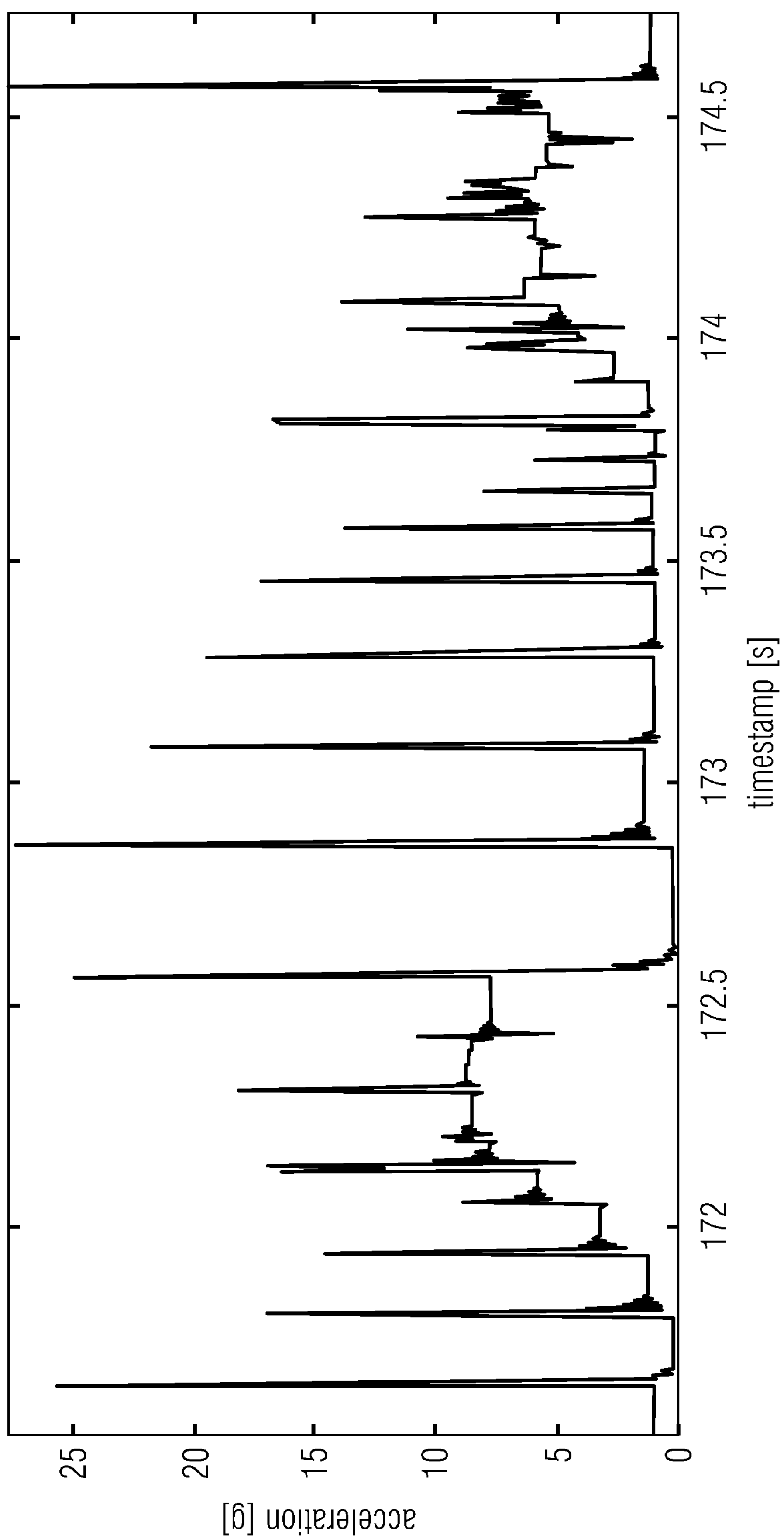
FIG. 9B shows an acceleration measurement diagram representing acceleration values obtained from an equipment module attached to a ball during a low/ground pass, according to an embodiment.
Figure 9C:
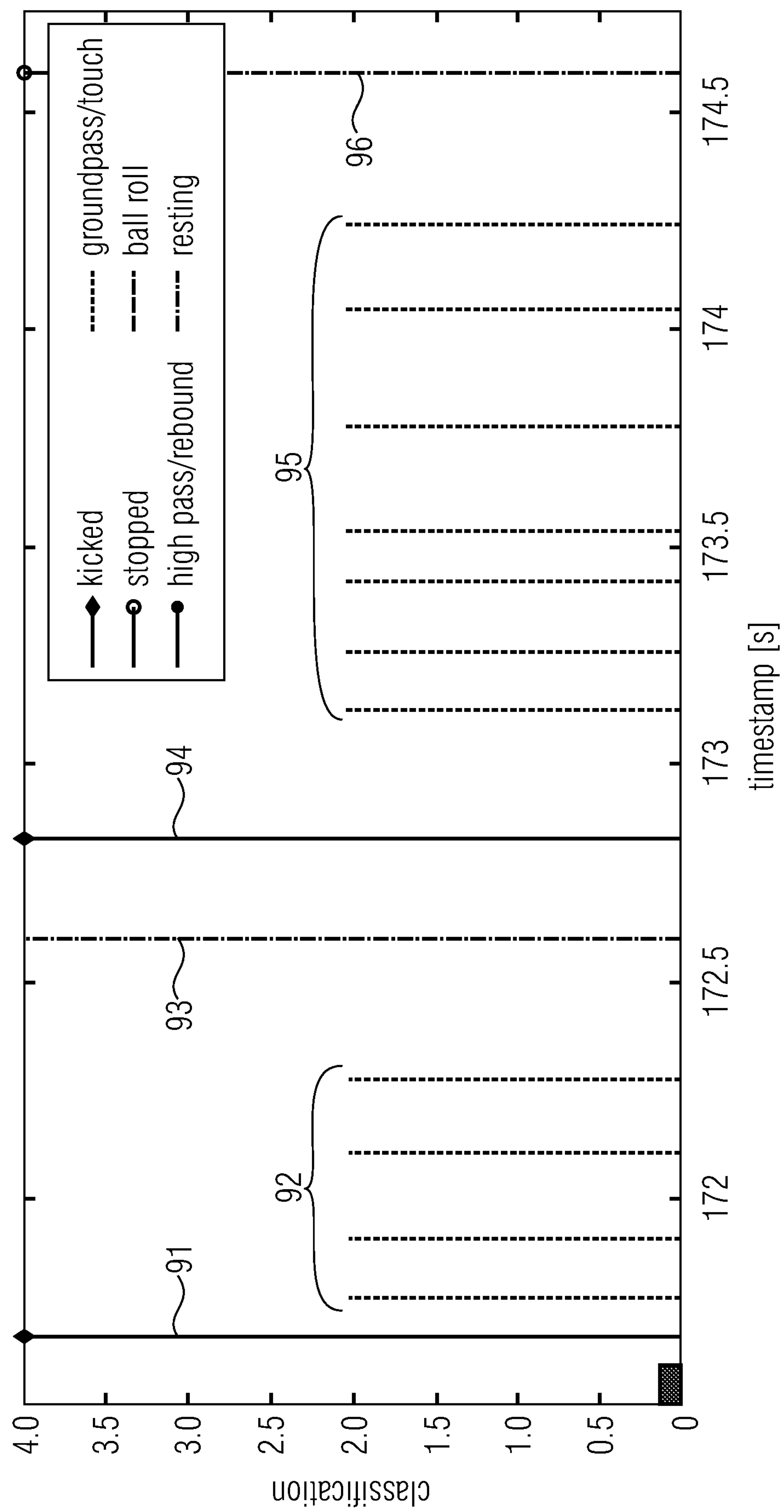
FIG. 9C shows a motion profile of the ball which motion profile was determined from the rotation measurement data and the acceleration measurement data, according to an embodiment.

FIGS. 9A, 9B and 9C show an example of equipment based data which has been collected while two players played low passes between each other. A low pass may in the following also be referred to as a ground pass. An equipment module was attached to the ball, wherein the equipment module comprised a sensor device comprising a rotation sensor and an acceleration sensor.

FIG. 9A shows the raw measurement data of the rotation sensor. FIG. 9B shows the raw measurement data of the acceleration sensor. Features were extracted and classified into physical ball events, as described above. These physical ball events are collected and combined in a motion profile, which is shown in FIG. 9C.

As can be seen at the time scale of the rotation diagram in FIG. 9A the rotation of the ball was steadily increasing. This may happen if the ball is rolling on the ground and steadily gains momentum after having been kicked, i.e. it rotates faster and faster.

As can be seen at the beginning of the time scale of the acceleration diagram in FIG. 9B, a first peak is detectable which can be extracted and classified as a physical ball event 91 (FIG. 9C) "ball was kicked". Further subsequent smaller peaks are detectable which may occur when the ball quickly and repeatedly touches the ground, which may be typical for a low pass. These consecutive peaks may be extracted and classified as a physical ball event 92 (FIG. 9C) "Ground Pass/Touch".

At about 172.6 seconds, a further peak may be detectable in the acceleration diagram (FIG. 9B) while an abrupt stop of rotation may at the same time be detected in the rotation diagram (FIG. 9C). This may happen when a player receives a ground pass and stops the ball. These features may be extracted and classified as a physical ball event 93 (FIG. 9C) "stopped".

Afterwards, a second ground pass was played by the two players. As can be seen in the motion profile shown in FIG. 9C, a further physical ball event 94 "ball was kicked" followed by consecutive physical ball events 95 "Ground Pass/Touch", followed by a further physical ball event 96 "stopped" were classified and inserted into the motion profile.

This motion profile may indicate that a low pass (i.e. ground pass) was played with the ball. A corresponding activity profile (not shown) of a player that may have kicked the ball may be fused with the motion profile (FIG. 9C) of the ball. Thereby, the computing unit 13 may determine a corresponding game scenario involving the player and the ball, namely that said player may have played the low pass.

A further activity profile of a further player module attached to a further player may be processed by the computing unit 13. This further activity profile may indicate that the further player may have received the low pass. Accordingly, the computing unit 13 may determine a corresponding game scenario involving both players and the ball, namely that a certain first player may have played the low pass to a certain second player.

Figure 10:
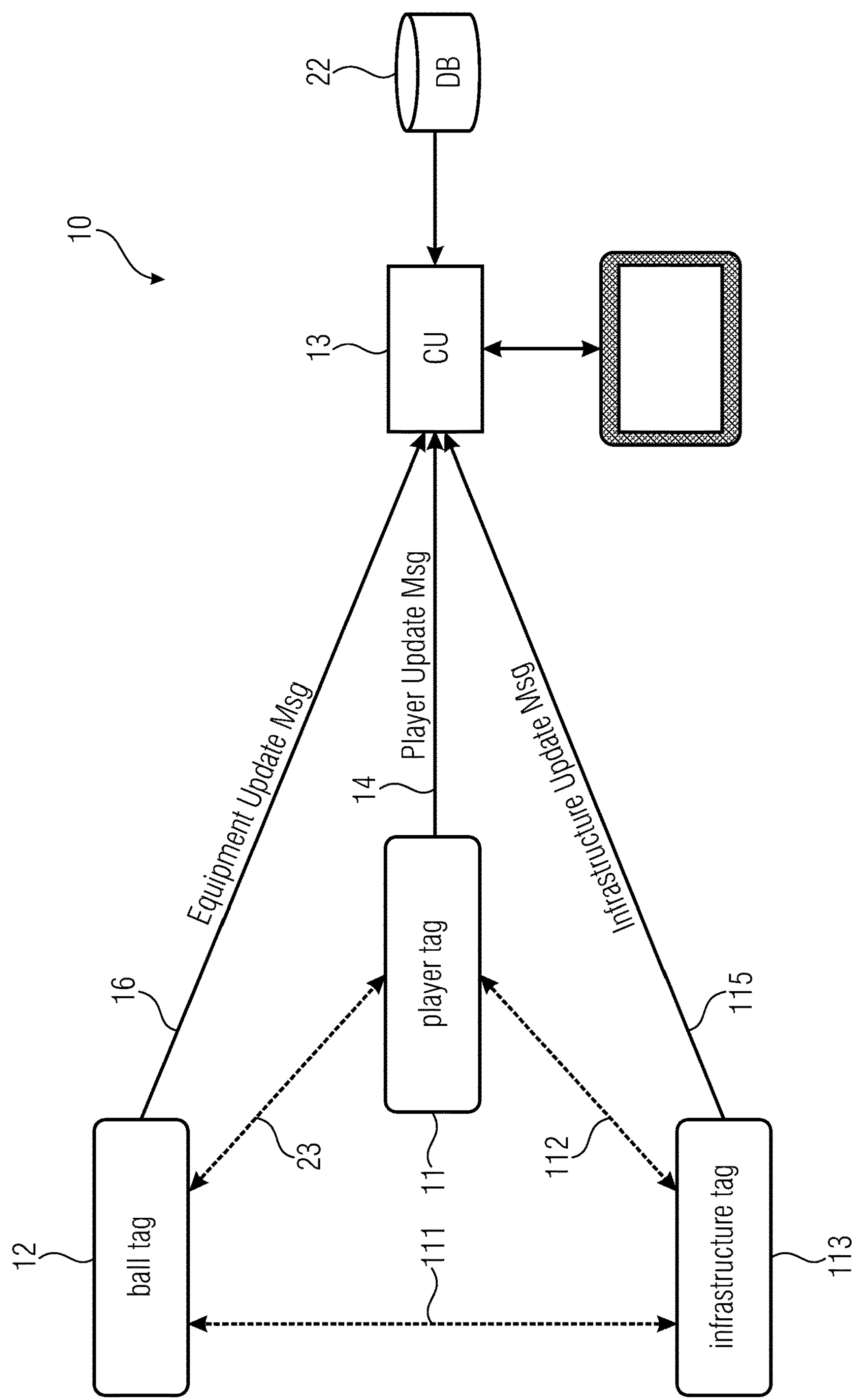
FIG. 10 shows a schematic overview of a further example of a communication infrastructure of an inventive system comprising an optional infrastructure module according to an embodiment.

A further embodiment of the inventive system 10 is schematically depicted in FIG. 10, which may show a similar configuration as previously described with reference to FIG. 2. Thus, regarding the elements which are contained in FIG. 2 it is referred to the corresponding description above.

However, in addition to FIG. 2 the system 10 may comprise a further module, namely an infrastructure module 113, also referred to as an infrastructure tag. Said infrastructure module 113 may be a mobile, or advantageously a stationary module being associated with the playing field on which the sports game takes place.

The infrastructure module 113 may comprise a communication interface for communicating, in a unidirectional or a bidirectional way, with at least one of the player module 11, the equipment module 12 and the computing unit 13. Additionally or alternatively, the infrastructure module 113 may be configured to perform an RSSI measurement in cooperation with the equipment module 12 via a channel 111, and/or to perform an RSSI measurement in cooperation with the player module 11 via a channel 112.

The infrastructure module 113 may generate infrastructure based data 115 which may be transmitted to the computing unit 13. The computing unit 13 may use the received infrastructure based data 115 in addition to the received player based data 14 and the received equipment based data 16 for determining the game scenario.

The infrastructure based data 115 may, in this non-limiting example, be contained in an Infrastructure Update Message, while the player based data 14 may be transmitted in a Player Update Message from the player module 11 to the computing unit 13, and/or while the equipment based data 16 may be transmitted in an Equipment Update Message from the equipment module 12 to the computing unit 13.

The Player Update Message, the Equipment Update Message and the Infrastructure Update Message may each comprise the same data structure.

FIG. 11 shows an example of a data structure of a respective Update Message, which may be valid for each of the Player Update Message, the Equipment Update Message and the Infrastructure Update Message. An Update Message may comprise a feature list comprising one or more features 14*b*, 16*b*, which may have been extracted as described above with reference to FIG. 6. Additionally or alternatively, it may comprise an event list comprising one or more physical events, which may have been classified/estimated as described above with reference to FIG. 6. Additionally or alternatively, it may comprise a Raw Data List comprising one or more of the raw sensor measurement data 14*a*, 16*a*, which may have been obtained by at least one of the sensor devices 17, 19 of a respective module 11, 12, 113.

Optionally, the respective Update Message may comprise an RSSI list comprising information concerning RSSI values between two or more modules or tags, which may include one or more player modules 11, and/or one or more equipment modules 12 and/or one or more infrastructure modules 113. Further optionally, it may comprise a Sender Compressed ID for identifying the sender of the message, and a Timestamp for synchronizing purposes.

Since the tags 11, 12 may be equipped with radio communication units, they can additionally make temporal measurement of the RSSI from one another. Since the RSSI values are dependent on both the distance and the position of the two tags 11, 12 between which the RSSI is measured, a tag 11, 12 can compute a rough distance estimate to another tag in the system 10. The tags 11, 12 can report a list of other tags from which they receive the signals with strongest RSSI. The list of RSSI measurement can be fused together with event detection at the tags 11, 12 themselves to e.g. further improve the determination of possession of the ball.

The computing unit 13 may additionally administer a database 22 (c.f. FIG. 2), whereby the database 22 can contain information on the playing positions of players, physical statistics, habits, event history of game or up to all classified earlier, or of the progress of the team.

By fusing the information about temporal possession of a ball, higher level training statistics such as successful passes or missed passes within a team may be generated. Other statistics may include but not limited to the frequency of passes between two members of a team, touch time, first touch precision and so forth.

Figure 12:
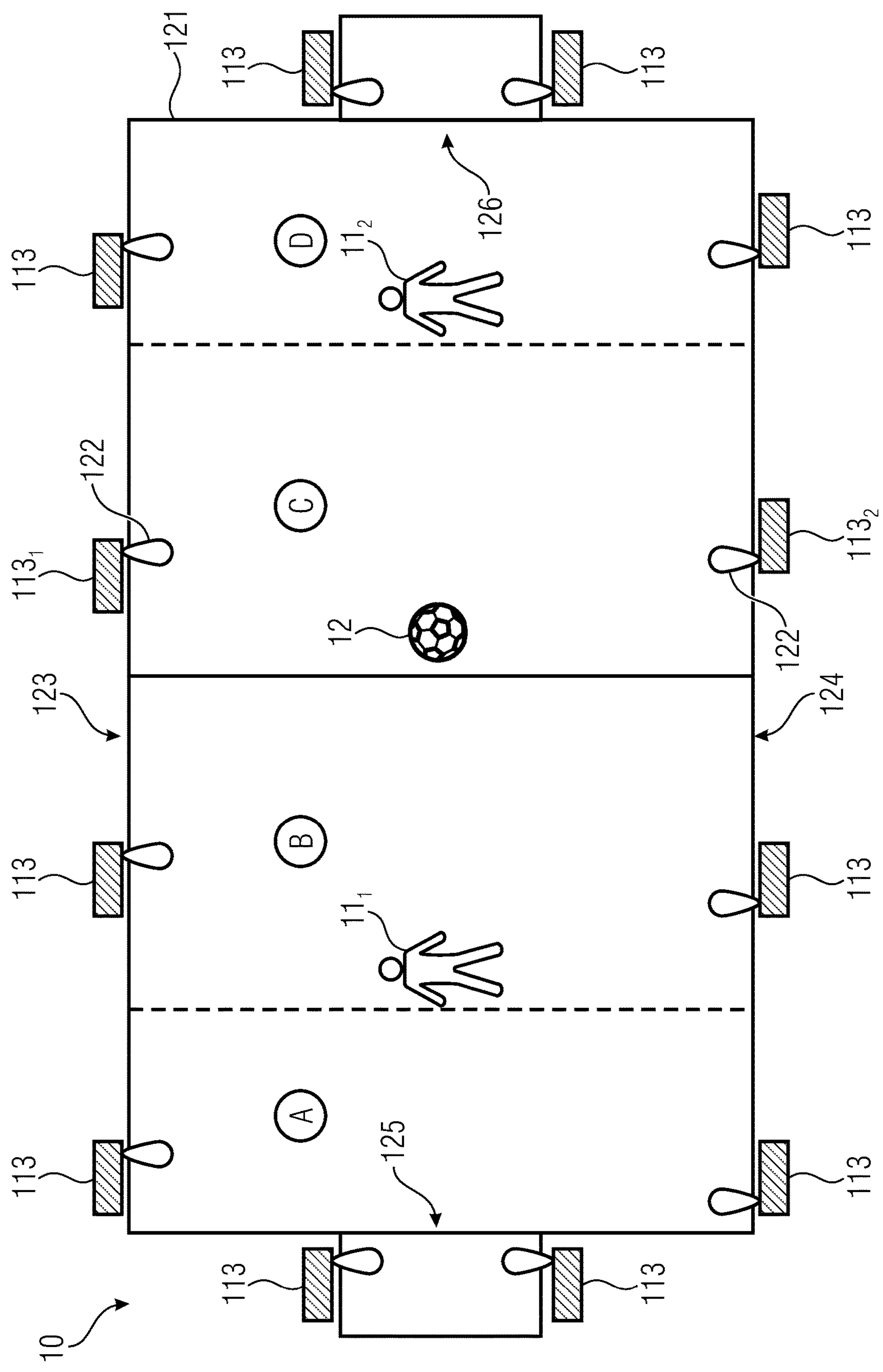
FIG. 12 shows a schematic overview of an example of a playing field in which the inventive system may be deployed according to an embodiment.

As mentioned above, the system 10 may comprise one or more infrastructure modules 113. FIG. 12 shows a non-limiting example of a system 10 comprising twelve infrastructure modules 113 being associated with a soccer playing field 121. Furthermore, a ball 12' comprising at least one equipment tag 12, a first player $\mathbf{11'}_1$ comprising at least one player module $\mathbf{11}_1$, and a second player $\mathbf{11'}_2$ comprising at least one further player module $\mathbf{11}_2$ are depicted as non-limiting examples.

According to an embodiment, at least one of the infrastructure modules 113 may be arranged inside, outside, at, on, over, under or around the playing field 121.

Additionally or alternatively, at least one of the infrastructure modules 113 may be associated with an installation belonging to said playing field 121. Such an installation may, for example, be a goal post of a soccer goal or a football goal, a rim of a basket of a basketball game, or the like. The at least one of the infrastructure modules 113 may be arranged inside, outside, at, on, over, under or around said installation of the playing field 121.

Again, the computing unit 13 may be configured to receive infrastructure based data 115 from the infrastructure module 113, and the computing unit 13 may be configured to combine the infrastructure based data 115 with the player based data 14 and with the equipment based data 16 for determining the game scenario. In this example, the determined game scenario may be a game scenario in which the player, the equipment and optionally the infrastructure may be involved. Accordingly, the computing unit 13 may determine a game scenario 18 based on the player based data 14 representing an activity profile 14*c* of the player 11' and on the equipment based data 16 representing a motion profile 16*c* of the equipment 12' and on the infrastructure based data 115.

At least one of the infrastructure modules 113 may comprise a directional antenna comprising a directional antenna pattern, which may also be referred to as a sectorized antenna. With reference to FIG. 12 each of the infrastructure modules 113 may comprise a directional antenna, wherein the directional antenna pattern is symbolized by means of the drop-shaped symbol 122.

According to an embodiment, at least one of the infrastructure modules 113 may comprise a directional antenna 122 being directed onto the playing field 121. For instance, at least one infrastructure module 113 may be arranged such that the directional antenna pattern 122 is directed orthogonal to a spatially nearest demarcation line of the playing field 121. For example, the upper four and lower four infrastructure modules 113 in FIG. 12 may be arranged along the side touch lines 123, 124 of the playing field 121. Thus, as regards these infrastructure modules 113 the respective side touch line 123, 124 is considered to be the spatially nearest demarcation line of the playing field 121.

As can be seen in FIG. 12, these infrastructure modules 113 are arranged such that the directional antenna pattern 122 is directed orthogonally to the respective side touch line 123, 124 of the playing field 121.

As can further be seen in FIG. 12, at least one infrastructure module 113 may be arranged in the goal area. According to this example, the at least one infrastructure module 113 may be arranged such that the directional antenna pattern 122 is directed parallel to a spatially nearest demarcation line of the playing field 121. In this example, the spatially nearest demarcation line would be the goal line 125, 126.

As can be seen in FIG. 12, these infrastructure modules 113 are arranged such that the directional antenna pattern 122 is directed parallel to the respective goal line 125, 126 of the playing field 121.

Additionally or alternatively, it may be possible that at least one infrastructure module 113 may be arranged such that the directional antenna pattern 122 is directed along a spatially nearest demarcation line of the playing field 121. For example, the at least one infrastructure module 113 may be arranged such that the directional antenna pattern 122 is directed along the side touch line 123, 124 or along the goal line 124, 125. Each sports game may have its individual demarcation lines, whereas the above described embodiments may be applied to any other sports different than the exemplarily described soccer game.

Accordingly, the playing field 121 itself may be equipped with one or more of the above described infrastructure tags 113. The infrastructure tags 113 may differ from the player tag 11 and/or ball tag 12 in a sense that they may be stationary for the duration of the game. In particular, the infrastructure tags 113 may be equipped with a directional antenna 122, as described above. The directional antenna 122 may serve at least one of two purposes—first they may serve to provide relative localization of player/ball tags 11, 12 in the playing field 121 with respect to the infrastructure tags 113, and second, they may serve to partially reduce interference from external radio (e.g. Bluetooth) devices that may be deployed nearby, for example by the spectators for their personal gadgets in the match, to ensure communication.

Due to the directional, i.e. sectorized, nature of the respective antennas 122, they may indicate whether the ball 12' may be out-of-field. This information may be further combined with the events that follow, such as throw or free kick, to generate statistics of the match.

Of particular interest here may be infrastructure tags 113 that may indicate whether the ball 12' may have crossed the goal line 125, 126, for example. The purpose of this technology is not primarily to make "goal" decisions on a match level, but rather to track the progress of a training session automatically. To this end, given that two infrastructure tags 113 may be placed at two sides of a respective goal post, the decision of whether or not the ball 12' may have entered the goalpost can be made by estimating the RSSI from the ball 12' at both of the infrastructure tags 113, or due to channel reciprocity, estimating the RSSI from both tags 113 at the ball 12' itself. The infrastructure tags 113 may also be referred to as anchors herein.

Figure 13:
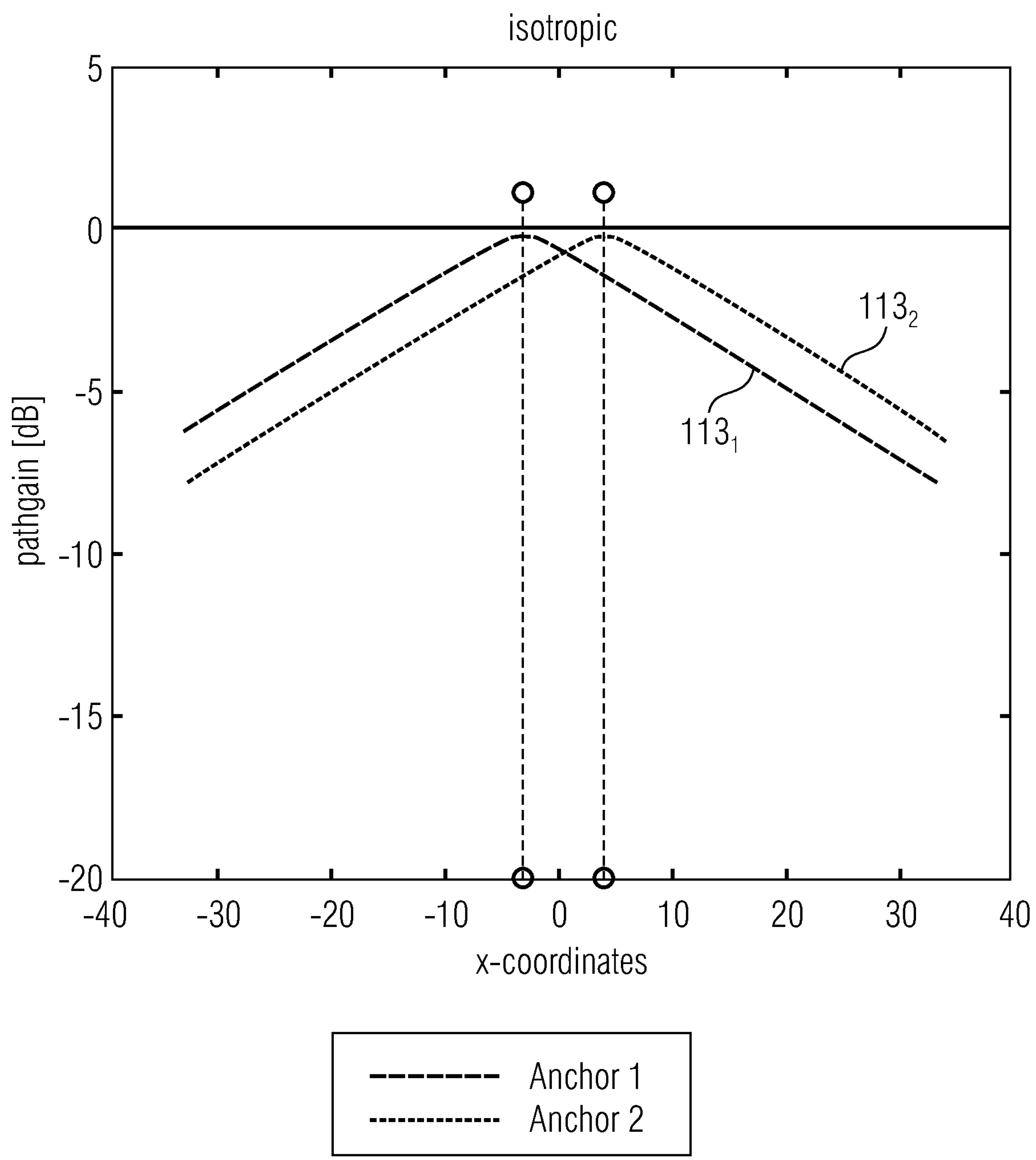
FIG. 13 shows an isotropic case of an RSSI path-loss measurement between a ball module and two infrastructure modules that are attached to the two goalposts of a soccer goal while the ball was moving past the infrastructure modules into the goal, according to an embodiment.
Figure 14:
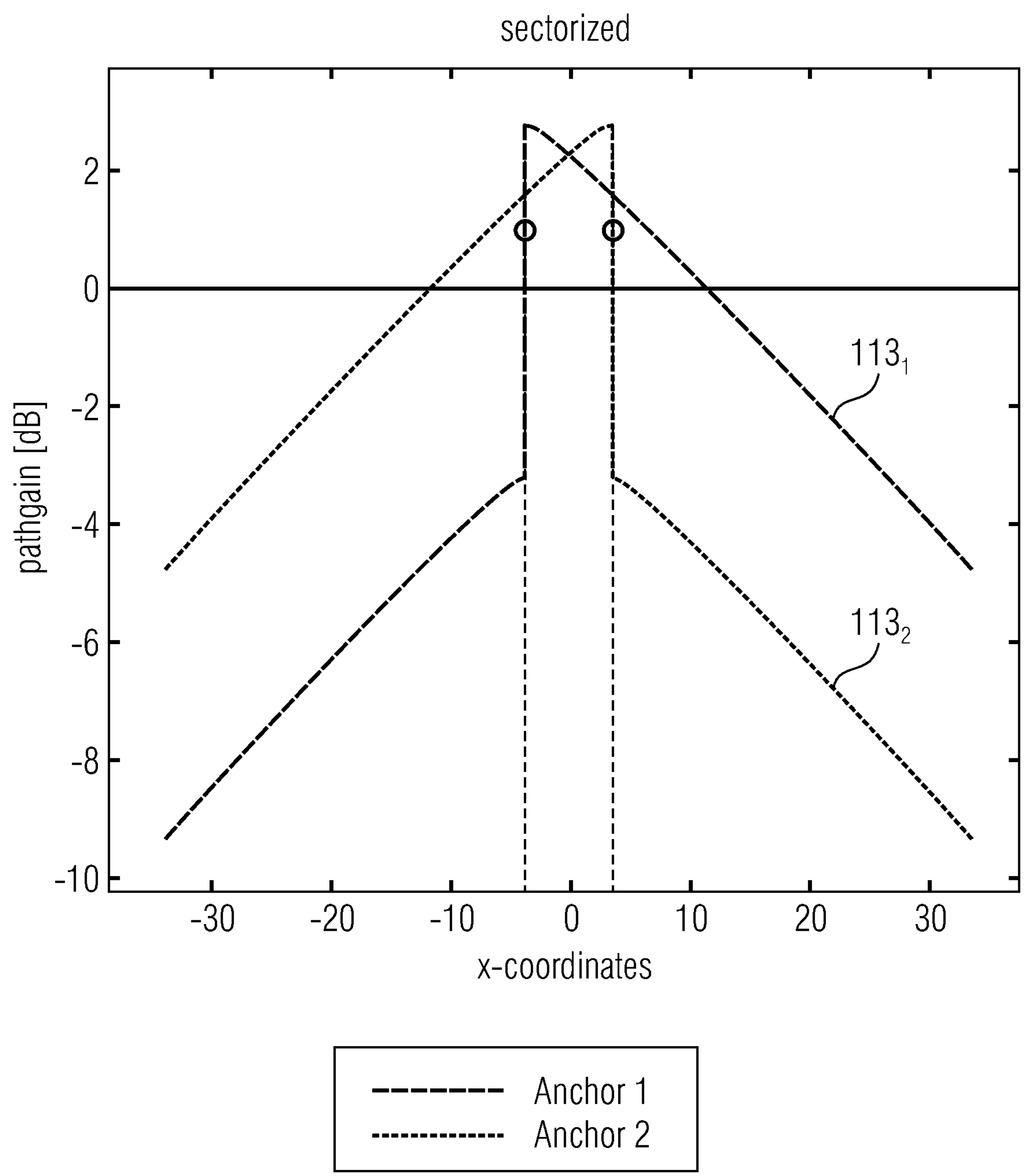
FIG. 14 shows a sectorized case of an RSSI path-loss measurement between a ball module and two infrastructure modules that are attached to the two goalposts of a soccer goal while the ball was moving past the infrastructure modules into the goal, according to an embodiment.

FIGS. 13 and 14 show a rough depiction of pathloss from two infrastructure tags $\mathbf{113}_1$, $\mathbf{113}_2$ to the ball 12'. The two infrastructure tags $\mathbf{113}_1$, $\mathbf{113}_2$ may also be referred to as Anchor 1 and Anchor 2. The two infrastructure tags $\mathbf{113}_1$, $\mathbf{113}_2$ were placed at the left and right goalpost, respectively.

FIG. 13 the measurement values of an isotropic case, i.e. using antennas comprising an isotropic antenna pattern. FIG. 14 shows the measurement values of a sectorized case, i.e. using antennas comprising a sectorized, i.e. directional antenna pattern. In the latter case, the infrastructure tags $\mathbf{113}_1$, $\mathbf{113}_2$ were mounted such that their respective directional antenna pattern 122 was directed parallel to the goal line 124, 125, as shown in FIG. 12.

In both cases, the infrastructure tags $\mathbf{113}_1$, $\mathbf{113}_2$ were mounted at a height of 1.66 m, which is half the goalpost size. The results as shown in FIG. 13 for an isotropic case, and in FIG. 14 for a sectorized case, are valid for a free space pathloss, and without taking log-normal shadowing into account.

The results show that both in the isotropic case (FIG. 13) and in the sectorized case (FIG. 14), the RSSI measured can be used to deduce whether the ball 12' has passed by the post or not. Using probabilistic models, the RSSI information and dynamics of the game can be fused to form a decision whether or not the goal has been made. However, using sectorized antennas comprising a directional antenna pattern may reveal more accurate and reliable results. Thus, the sectorized antennas may advantageously be used in the infrastructure modules 113.

Figure 15:
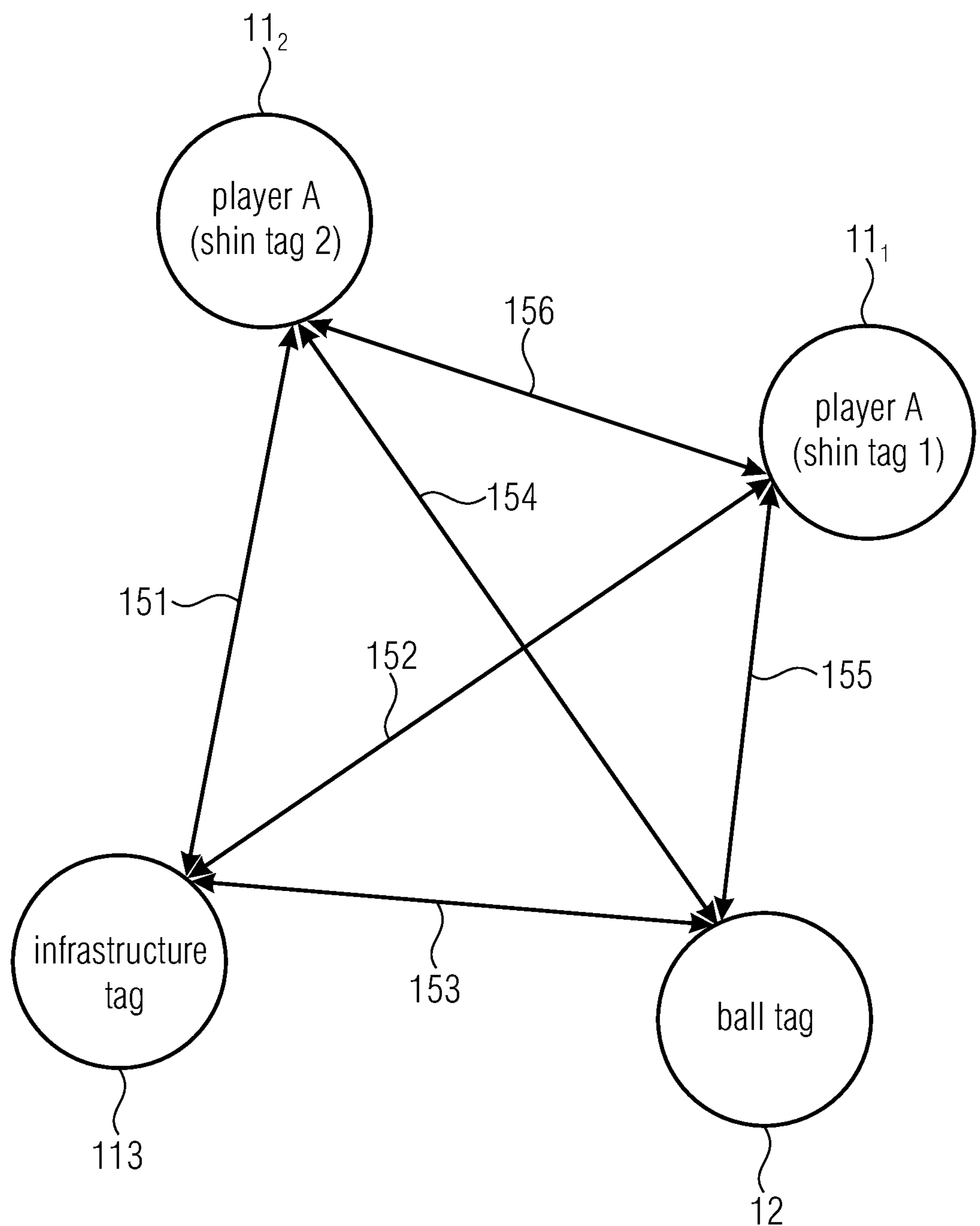
FIG. 15 shows a schematic overview of a communication network comprising one or more player modules, one or more equipment modules and optionally one or more infrastructure modules, according to an embodiment.

As shown in FIG. 15, the RSSI measurements may be performed cooperatively between one or more player tags $\mathbf{11}_1$, $\mathbf{11}_2$, one or more equipment tags 12 and optionally one or more infrastructure tags 113. That is, the infrastructure tags 113 may be configured to measure an RSSI value of a signal received from at least one of the player tags $\mathbf{11}_1$, $\mathbf{11}_2$ and the equipment tag 12, as indicated by arrows 151, 152, 153 pointing to the infrastructure tag 113. In turn, the player tags $\mathbf{11}_1$, $\mathbf{11}_2$ and/or the equipment tags 12 may be configured to measure an RSSI value of a signal received from the infrastructure tag 113, as indicated by the arrows 151, 152, 153 pointing to the player tags $\mathbf{11}_1$, $\mathbf{11}_2$ and the equipment tag 12.

The simplified graphic of FIG. 15 shows the possible RSS measurements between all network members $\mathbf{11}_1$, $\mathbf{11}_2$, 12, 113 which may be indicated by the two-sided double arrows 151, 152, 153, 154, 155, 156, where the two sides highlight the fact that each tag can function as both a transmitter and a receiver Based on at least one of the above mentioned RSSI values, at least one of the player tags $\mathbf{11}_1$, $\mathbf{11}_2$, the equipment tag 12 and the infrastructure tag 113 may be configured to calculate an absolute position of the respective player tag $11_1$, $11_2$ and/or of the equipment tag 12 on the playing field 121. For example, an absolute position at the playing field in the range of decimeters or centimeters may be calculated for at least one of the respective player module $11_1$, $11_2$ and the equipment module 12.

Since the players 11', the ball 12' and the infrastructure tags 113 may all communicate via a radio technology like—but not limited to—Bluetooth, the Received Signal Strengths (RSS) between each member of the network, i.e. between each tag 11, 12, 113, may be calculated at any time. If no stationary infrastructure tags 113 may be available, the approach may be a swarm like one with all other tags 11, 12 being mobile, which will be discussed further below. As RSS propagation is distance-dependent, information on the relative positions of all members 11, 12, 113 of the network can be obtained this way.

For a network with n members, up to n(n−1) RSS between all members 11, 12, 113 of the network may be observed (note that the RSS from network member A to network member B may not be the same as from member B to member A due to different antenna patterns) at each time instant. FIG. 15 shows a simplified network of this type, wherein a first player tag $11_1$ may be attached to the left shin of a player, a second player tag $11_2$ may be attached to a right shin of the same player, an equipment tag 12 may be attached to a ball 12', and an infrastructure tag 113 may be arranged at the playing field 121. Each of the first and second player tags $11_1$, $11_2$, the equipment tag 12 and the infrastructure tag 113 may be network members.

For example, in a typical soccer game with eleven players per team, with two tags for each player of each team, one ball tag and four stationary infrastructure tags, 2346 measurements may be available at once. The number of states, e.g. two-dimensional positions of all players and the ball with 46, is relatively small in comparison, yielding an overdetermined system of equations. An exemplary simplified model of the measured RSS $RSS_{ab}$ of a signal sent from a network member a (in the role of the source/transmitter) located at $p_a$ to another member b (in the role of a receiver) located at $p_b$, dependent on their Euclidean distance $d_{ab}$ in logarithmic form, e.g. in dBm can be described by:

$$RSS_{ab}(p_a, p_b) = RSS_0 - 10\ \gamma\log_{10}\left(\frac{d_{ab}}{d_v}\right) + \mathcal{J}_{fad,a}(p_a, p_b),$$

Where $\gamma$ denotes the path-loss parameter ($\gamma$=2 in free space), $RSS_0$ denotes the RSS at a reference distance e.g. 1 m and $\sigma_{fad,a}(p_b)$ describes the log-normal shadow-fading component at $p_a$, which is modeled as random, but spatially correlated, and therefore also exhibits a dependency on the positions of both tags (this dependency is reduced to only b if tag a is stationary).

Now these measurements, or any subset of them, may be used to estimate the states of interest: the positions of the ball 12' and/or the players 11' (or any subset of those) within the playing field 121, which may be defined by the infrastructure tags 113, or a relative position with respect to at least one of the tags 11, 12 if no infrastructure tag 113 with known positions within the playing field 113 may be available.

For example, this can be done by using Bayesian filters like Kalman or particle filters, least squares methods, and using the model mentioned above or another deterministic or stochastic model for RSS propagation (e.g. Ray-Tracing). Furthermore, additional information obtained by the system 10 (e.g. alignment of the position of the ball 12' and a player 11' based on ball contact information, obtained motion state information on the player 11' (running, dribbling, stopping), raw IMU data or kinematic information) and additional available meta-information (e.g. a player's team position, e.g. goalkeeper, defense player, etc. or input regarding technical formations of players e.g. 4-4-2, game events (corner kick, free kick, penalty kick, kickoff, throw-in, etc.), information on the expected velocity and movement of a soccer athlete) can be used in the filter e.g. for transition modeling or a-priori probability distributions. In addition, observations of the RSS at known positions (called "Fingerprints") may be used in the solution e.g. as part of a measurement model, especially to model the fading component.

According to yet a further exemplary embodiment, the playing field 121 may be segmented into a plurality of segments, for instance by means of a plurality of rectangles, wherein the absolute position in terms of segments may be calculated for at least one of the respective player modules $11_1$, $11_2$ and the equipment module 12.

As one non-limiting example, it shall be referred back to FIG. 12. As can be seen, two infrastructure modules, indicated with reference numerals $113_1$ and $113_2$, may be arranged oppositely to one another, for instance, a first infrastructure tag $113_1$ may be arranged at a first side touch line 123 and a second infrastructure tag $113_2$ may be arranged at an opposite second side touch line 124. Each of the infrastructure tags $113_1$, $113_2$ may comprise a sectorized antenna comprising a directional antenna pattern, wherein both antenna patterns may be directed towards each other.

Thereby, the playing field 121 may be segmented into a plurality of segments. In this example, the first and second infrastructure modules $113_1$, $113_2$ may create a segment 'C' which may be one of a plurality of segments 'A', 'B', 'C' and 'D'. For example, the ball 12' may be located in segment 'C', the first player $11'_1$ may be located in segment 'B' and the second player $11'_2$ may be located in segment 'D'.

In any of the above described exemplary embodiments, at least one of the infrastructure module 113, the player module 11, the equipment module 12 and the computing unit 13 may be configured to calculate, based on the measured RSSI value, a relative spatial distance between the infrastructure module 113 and at least one of the player module 11 and the equipment module 12.

Additionally or alternatively, in any of the above described exemplary embodiments, at least one of the infrastructure module 113, the player module 11, the equipment module 12 and the computing unit 13 may be configured to calculate, based on the measured RSSI value, an absolute position of at least one player module 11 and/or at least one equipment module 12 at the playing field 121.

Accordingly, the above described localization of at least one player 11' and/or at least one equipment 12' at the playing field 121 may be supported by one or more infrastructure tags 113.

However, in yet a further exemplary embodiment, it may be possible that a localization of at least one player 11' and/or at least one equipment 12' may be performed without RSSI measurement values being associated with one or more infrastructure modules 113. In other words, it may be possible that a localization of at least one player 11' and/or at least one equipment 12' may be performed with RSSI measurement values being associated with at least one player tag 11 and/or at least one equipment tag 12. According to such embodiments, a localization of at least one player 11' and/or at least one equipment 12' may be possible even without any infrastructure tags 113.

Such an embodiment may correspond to the one as depicted in FIG. 15, possibly without the infrastructure tag 113. Such an approach of RSSI localization between the movable one or more player modules $11_1$, $11_2$, and/or the movable equipment module 12 may be referred to as a RSSI swarm localization or RSSI cooperative localization, wherein the RSS may be calculated as described above but without infrastructure tags 113 as network members.

According to such an embodiment, at least one player module $11_1$, $11_2$ may be configured to measure a Received Signal Strength Indication—RSSI—value of a signal received from the equipment module 12. Additionally or alternatively, the equipment module 12 may be configured to measure a Received Signal Strength Indication—RSSI—value of a signal received from the at least one player module $11_1$, $11_2$.

Based on said measured RSSI value, the at least one player module $11_1$, $11_2$ and/or the equipment module 12 and/or the computing unit 13 may be configured to calculate a relative spatial distance between the at least one player module $11_1$, $11_2$ and the equipment module 12.

Additionally or alternatively, based on said measured RSSI value, the at least one player module $11_1$, $11_2$ and/or the equipment module 12 and/or the computing unit 13 may be configured to calculate an absolute position of the at least one player module $11_1$, $11_2$ and the equipment module 12 on the playing field 121.

For example, the ball module 12' and the player modules $11_1$, $11_2$ may have a radio, e.g. a Bluetooth, data connection. With the radio (e.g. Bluetooth) capability an RSSI (signal strength) measurement can be made by the respective player/equipment modules $11_1$, $11_2$, 12 and be used to estimate the distance between the modules $11_1$, $11_2$, 12, which distance may be a relative distance between the modules $11_1$, $11_2$, 12 from which a relative position of the modules $11_1$, $11_2$, 12 among each other may be determined/estimated. Combining all distance estimates a situation picture can be created including estimates of player and ball positions. This may also allow to determine an absolute position of the modules $11_1$, $11_2$, 12 on the playing field 121.

If RSSI measurement data may be available on, in best case all modules $11_1$, $11_2$, 12, a relative distance between all modules $11_1$, $11_2$, 12 can be estimated and this information can be fused to improve the accuracy of the distance estimates and furthermore to localize the modules $11_1$, $11_2$, 12 relative to each other in a swarm like approach, even if no infrastructure tags 113 may be available.

However, this may be improved by using modules (e.g. infrastructure modules 113) at fix and known positions, as described above.

The computing unit 13 may receive said measured one or more RSSI values from a player module 11 and/or an equipment module 12, and the computing unit 13 may use these one or more RSSI values together with the player based data 14 representing an activity profile of the player 11' and the equipment based data 16 representing a motion profile of the equipment 12' and optionally with infrastructure based data 155, if available, for determining a game scenario 18.

In other words, according to an embodiment, the computing unit 13 may be configured to receive an RSSI value from at least one of the player module 11 and the equipment module 12, and to determine, based on the activity profile 14*c* of the player 11' and on the motion profile 16*c* of the equipment 12' and on the received RSSI value, the one of a plurality of game scenarios 18 involving the player 11' and the equipment 12'.

For example, the RSSI value may be used in order to determine which player on the field may have kicked a ball, for instance if two or more players are positioned close to each other. For example, in a duel between a first player $11'_1$ comprising a first player module $11_1$ and a second player $11'_2$ comprising a second player module $11_2$, the first player $11'_1$ may kick the ball while the second player $11'_2$ may unintentionally kick into the grass. Both player modules $11_1$, $11_2$ may generate an acceleration signal which may be very similar. However, the RSSI value may indicate that the ball was closer to the first player $11'_1$ than to the second player $11'_2$.

For this, the RSSI values associated with the first player module $11_1$ and the RSSI value associated with the second player module $11_2$ may be compared with each other. For example, if the result of comparing the RSSI values may reveal that the first player module $11_1$ comprises a lower spatial distance to the ball 12' than the second player module $11_2$, then this may be an indication that the first player $11'_1$ was closer to the ball 12' than the second player $11'_2$. Thus, there is a higher probability that the first player $11'_1$ may have kicked the ball 12'.

Based thereon, the computing unit 13 may determine, for instance, a game scenario "won duel" of the first player $11'_1$ based on the player based data 14 of the first player $11'_1$ (activity profile) and on the equipment based data 16 (motion profile) and on the RSSI values.

In more general terms, the computing unit 13 may be configured to receive a first RSSI value being related with a first player module $11_1$ and a second RSSI value being related with a second player module $11_2$, wherein the computing unit 13 may further be configured to compare the first and the second RSSI values and to take the player based data 14 of the first player module $11_1$ for determining the game scenario if the result of comparing the RSSI values indicates that the first player module $11_1$ comprises a lower spatial distance to the equipment 12 than the second player module $11_2$.

The information of the inventive concept above can be fused, e.g. the dynamics of the modules $11_1$, $11_2$, 12 can help here, e.g. velocity near zero, high speed movement, high dynamic movement, information on ball possession, etc.

In the estimation process additionally to distances and positions e.g. RSSI-measurement offsets and non-linearities, channel parameters of the propagation channel can be estimated (e.g. path loss coefficient, shadowing, log-normal fading, method Kriging).

Such an RSSI cooperative localization may comprise the following advantages:

- One of the cheapest localization systems realizable
- Inexpensive: Use of low-cost communication (Bluetooth or WiFi) compared to tracking systems with high-speed cameras or precise radiolocation
- Reuse of communication infrastructure
- No installation effort for infrastructure
- HW-Components would be already available with the inventive system above
- Combination with game events from inventive system increases meaningfulness of statistics, e.g. where on the field and in which situation passes were successful or not In the following the inventive concept shall briefly be explained and summarized again in some other words.

Objective data to measure an athlete performance in a team-sport scenario such as football or soccer may be valuable information for coaches and athletes themselves for improving performance at individual level and/or team level. To this end, statistics such as successful and missed passes from one athlete to another, passing speed, type of pass (high/low), possession of the ball, motion dynamics of the ball, performance of athletes and so on need to be generated.

To generate the statistics, measurements could be made by attaching modules 11, 12 (herein also referred to as tags, or—depending on the attaching position—as a player module 11 or an equipment module 12) advantageously equipped with sensors 17, 19 and wireless communication capability to various entities (such as players 11', ball 12', boundary) in the game. An open problem is to obtain and optimally combine such measurements to generate the required statistics. At the same time, the solution may also be portable, affordable, power-efficient, scalable and resilient to external disturbances.

Thus, the inventive concept may suggest to put a module 12 in the ball 12' and have player modules 11, too. In contrast to known technology it becomes possible to detect that a player 11' might have kicked a ball 12', the ball 12' might have been kicked and later a player 11' may have accepted a ball 12' and the ball 12' might have been accepted by another player 11'. Combining these information the estimation of passes from player A to player B will be of much higher accuracy, than using e.g. just a player module, and much cheaper than using precise positioning. It is easier to distinguish successful and unsuccessful passes even if more players and balls are involved, like in a training scenario.

The proposed system may comprise the following components as shown in FIG. 2:

1) One active tag attached to the ball 12' (ball tag 12)
2) At least one active tag attached to the player 11' (player tag 11)
3) One or more computing units 13 (computing unit) and
4) At least one visualization unit 21 (APPs+GUI)
5) Database 22 that contains relevant information for the classification of events from the measured sensor data and other information, like decision domains The inventive concept may briefly be summarized in the following bullet points as follows:

1. Using modules 11, 12 with motion sensors 17, 19, like inertial sensors, magnetometers, and/or pressure sensors and a data connection between each other or with a central unit 13, together with methods to analyze the data and e.g. estimate passes from player A to player B, including feature extraction and decision trees and/or machine learning, whereas at least one module 12 may be integrated in a ball 12' and at least one module 11 may be attached to at least one player 11'.

Using the methods mentioned above events may be classified for each tag 11, 12 separately and the obtained information may be fused both in between the tags 11, 12 and using additional information e.g. from a database 22 to generate higher level information.

The Database 22 can contain information on the playing positions of players (goal keeper, defense, offense, etc.), physical statistics, habits, event history of game or up to all classified earlier events, or of the progress of the team.

The higher level information is e.g. pass from player A to player B, un/successful pass, time of ball possession, first touch precision, un/successful interception, won/lost duel, and statistics and analysis based on these
2. If RSSI or distance measurement data is available on at least some of the modules 11, 12, including the central units 13, the mentioned higher level information can be improved by including RSSI measurement data to e.g. estimate the distance between tags 11, 12, especially between player tags 11 and ball tags 12.
3. RSSI cooperative localization Idea: The ball modules 12 and player modules 11 may have a Bluetooth data connection. With the Bluetooth modules RSSI (signal strength) measurements can be made and used to estimate the distance in between modules 11, 12. Combining all distance estimates a situation picture can be created including estimates of player and ball positions.

So, if RSSI measurement data is available on in best case all modules 11, 12, a distance between all modules 11, 12 can be estimated and this information can be fused to improve the accuracy of the distance estimates and furthermore to localize the modules 11, 12 relative to each other in a swarm like approach.

This can be improved by using modules (e.g. infrastructure modules 113) at fix and known positions.

The information of the inventive concept above can be fused:

The dynamics of the modules 11, 12 can help here, e.g. velocity near zero, high speed movement, high dynamic movement, etc.

Information on ball possession can help here

In the estimation process additionally to distances and positions e.g. RSSI-measurement offsets and non-linearities, channel parameters of the propagation channel can be estimated (e.g. path loss coefficient, shadowing, log-normal fading, method Kriging).

Instead of a player tag 11 fixed to a player 11', a tag 12 can be fixed to an object, like a bottle, a bar, a goal, a bouncer and the like. Then, it can be monitored on the tag 12 by analysis of sensor data, if e.g. the target has been hit.

Furthermore, an inventive system 10 may be provided, the system 10 for determining a game scenario 18 in a sports game, the system 10 comprising at least one player module 11 configured to be attached to a player 11' of the game, at least one equipment module 12 configured to be attached to a sports equipment (e.g. ball, puck) 12' to be used in said game, and a computing unit 13, the player module 11 comprising a first sensor device 17 comprising at least a multi-axis accelerometer, a signal processing unit for determining a parameter (e.g. extracting a feature) **14*b* from raw sensor measurement data 14*a* received from the first sensor device 17 and for classifying said feature 14*b* into a physical player event (for determining an activity profile 14*c* of the player 11'), and a radio communication device for transmitting the physical player event/and or the activity profile 14*c* to the computing unit 13, the equipment module 12 comprising a second sensor device 19 comprising at least a multi-axis accelerometer, a signal processing unit for determining a parameter (e.g. extracting a feature) 16*b* from sensor measurement data 16*a* received from the second sensor device 19 and for classifying said feature 16*b* into a physical equipment event (for determining a motion profile of the equipment 12'), and a radio communication device for transmitting the physical equipment event and/or the motion profile 16***c* to the computing unit 13, the computing unit 13 comprising a radio communication device for receiving the physical player event and/or the activity profile 14*c* from the player module 11 and the physical equipment event and/or the motion profile 16*c* from the equipment module 12, and further comprising a classifier 68 for classifying the physical player event and/or the activity profile 14*c* together with the physical equipment event and/or the motion profile 16*c* into a game scenario 18.

In the following some non-limiting examples of game scenarios may be given, wherein a game scenario may comprise at least one of the group comprising a low pass played by a player, a high pass played by a player, a successful pass reaching another player from the same team, an unsuccessful pass reaching another player from a different team, a won or lost duel between two or more players, a penalty kick executed by a player, a corner kick executed by a player, a throw-in executed by a player, a volley shot executed by a player, a half-volley shot executed by a player, a header shot executed by a player, a dribbling executed by a player, a duration of ball possession by a player.

The inventive system 10 may provide the following advantages:

- Inexpensive: Use of low-cost sensors (<50 €) compared to tracking systems with high-speed cameras or precise radiolocation
- Player and game device (e.g. ball) metrics and events, as tags can be integrated into footballs and into other gaming devices
- Pre-processing of the data on the tag (signal/data analysis and event detection and processing). Therefore, significantly lower requirements arise on:
  - The latency due to the radio communication
  - The amount of data to be transferred via radio communication
  - The synchronization of the tags
- Higher robustness and higher functionality compared to systems where only player tag metrics are evaluated, as the player events can be correlated with the ball events and complemented by the ball events.

The inventive system 10 may be used in

- Analysis in sports, measure survey, state determination, state classification, information fusion, event recognition, event processing, (localization, location, tracking, communication),
- Sports: All ball sports, hockey, general sports with special equipment and one or more players interacting with it
- Training purposes and game analysis
- Digitalization of training sessions and games for later analysis or further processing Although some aspects have been described in the context of an apparatus, it is clear that these aspects also represent a description of the corresponding method, where a block or device corresponds to a method step or a feature of a method step. Analogously, aspects described in the context of a method step also represent a description of a corresponding block or item or feature of a corresponding apparatus. Some or all of the method steps may be executed by (or using) a hardware apparatus, like for example, a microprocessor, a programmable computer or an electronic circuit. In some embodiments, one or more of the most important method steps may be executed by such an apparatus.

Depending on certain implementation requirements, embodiments of the invention can be implemented in hardware or in software or at least partially in hardware or at least partially in software. The implementation can be performed using a digital storage medium, for example a floppy disk, a DVD, a Blu-Ray, a CD, a ROM, a PROM, an EPROM, an EEPROM or a FLASH memory, having electronically readable control signals stored thereon, which cooperate (or are capable of cooperating) with a programmable computer system such that the respective method is performed. Therefore, the digital storage medium may be computer readable.

Some embodiments according to the invention comprise a data carrier having electronically readable control signals, which are capable of cooperating with a programmable computer system, such that one of the methods described herein is performed.

Generally, embodiments of the present invention can be implemented as a computer program product with a program code, the program code being operative for performing one of the methods when the computer program product runs on a computer. The program code may for example be stored on a machine readable carrier.

Other embodiments comprise the computer program for performing one of the methods described herein, stored on a machine readable carrier.

In other words, an embodiment of the inventive method is, therefore, a computer program having a program code for performing one of the methods described herein, when the computer program runs on a computer.

A further embodiment of the inventive methods is, therefore, a data carrier (or a digital storage medium, or a computer-readable medium) comprising, recorded thereon, the computer program for performing one of the methods described herein. The data carrier, the digital storage medium or the recorded medium are typically tangible and/or non-transitory.

A further embodiment of the inventive method is, therefore, a data stream or a sequence of signals representing the computer program for performing one of the methods described herein. The data stream or the sequence of signals may for example be configured to be transferred via a data communication connection, for example via the Internet.

A further embodiment comprises a processing means, for example a computer, or a programmable logic device, configured to or adapted to perform one of the methods described herein.

A further embodiment comprises a computer having installed thereon the computer program for performing one of the methods described herein.

A further embodiment according to the invention comprises an apparatus or a system configured to transfer (for example, electronically or optically) a computer program for performing one of the methods described herein to a receiver. The receiver may, for example, be a computer, a mobile device, a memory device or the like. The apparatus or system may, for example, comprise a file server for transferring the computer program to the receiver.

In some embodiments, a programmable logic device (for example a field programmable gate array) may be used to perform some or all of the functionalities of the methods described herein. In some embodiments, a field programmable gate array may cooperate with a microprocessor in order to perform one of the methods described herein. Generally, the methods may be performed by any hardware apparatus.

The apparatus described herein may be implemented using a hardware apparatus, or using a computer, or using a combination of a hardware apparatus and a computer.

The methods described herein may be performed using a hardware apparatus, or using a computer, or using a combination of a hardware apparatus and a computer.

While this invention has been described in terms of several embodiments, there are alterations, permutations, and equivalents which fall within the scope of this invention. It should also be noted that there are many alternative ways of implementing the methods and compositions of the present invention. It is therefore intended that the following appended claims be interpreted as including all such alterations, permutations and equivalents as fall within the true spirit and scope of the present invention.

The invention claimed is:

1. A system for determining a game scenario in a sports game, the system comprising a player module being attachable to a player, an equipment module being attachable to a sports equipment to be used in said sports game, and a computing unit for receiving player based data from the player module and equipment based data from the equipment module, the player based data representing an activity profile of the player and the equipment based data representing a motion profile of the equipment, wherein the player module comprises a player sensor device configured to provide raw measurement data associated with the player to which the player module is attached, wherein the player module is configured to perform a feature extraction of the raw measurement data for determining, based on one or more extracted features, one or more physical events being executable by the player, wherein the player module is configured to determine the activity profile of the player based on the extracted one or more features and/or based on the determined one or more physical events, and to transmit the activity profile as the player based data to the computing unit, and/or to transmit the extracted one or more features and/or the determined one or more physical events to the computing unit for determining the activity profile of the player, wherein the equipment module comprises an equipment sensor device configured to provide raw measurement data associated with the equipment to which the equipment module is attached, wherein the equipment module is configured to perform a feature extraction of the raw measurement data for determining, based on one or more extracted features, one or more physical events being executable by or exertable on the equipment, wherein the equipment module is configured to determine the motion profile of the equipment based on a plurality of consecutive features and/or based on a plurality of consecutive physical events, and to transmit the motion profile as the equipment based data to the computing unit, and/or to transmit the plurality of consecutive features and/or the plurality of consecutive physical events to the computing unit for determining the motion profile of the equipment, wherein the player module is configured to determine the player based data during a predetermined time window, and wherein the equipment module is configured to determine the equipment based data during a predetermined time window, and wherein the computing unit is configured to timely synchronize the received player based data and the received equipment based data such that the time windows of the player based data and of the equipment based data at least partially overlap in a time domain, and wherein the computing unit comprises a Game Scenario Classification Stage that is configured to combine the activity profile of the player with the motion profile of the equipment so as to classify the activity profile of the player and the motion profile of the equipment into one of a plurality of game scenarios involving the player and the equipment.

2. The system of claim 1, wherein the player sensor device comprises at least one of a multi-axis accelerometer, an angular rate sensor, a magnetometer and a pressure sensor, the multi-axis accelerometer being configured to provide the raw measurement data representing an acceleration of a body part of the player to which the player module is attached, the angular rate sensor being configured to provide the raw measurement data representing a rotation of a body part of the player to which the player module is attached, the magnetometer being configured to provide the raw measurement data representing a value of the earth's magnetic field, and the pressure sensor being configured to provide the raw measurement data representing a pressure exerted by or at a body part of the player to which the player module is attached.

3. The system of claim 1, wherein the equipment sensor device comprises at least one of a multi-axis accelerometer, an angular rate sensor, a magnetometer and a pressure sensor, the multi-axis accelerometer being configured to provide the raw measurement data representing an acceleration of the equipment to which the equipment module is attached, the angular rate sensor being configured to provide the raw measurement data representing a rotation of the equipment to which the equipment module is attached, the magnetometer being configured to provide the raw measurement data representing a value of the earth's magnetic field, and the pressure sensor being configured to provide the raw measurement data representing a pressure exerted on the equipment to which the equipment module is attached.

4. The system of claim 1, further comprising a database configured to store additional information about at least one of the player, the equipment, and a temporal history of the game, wherein the computing unit is configured to retrieve said additional information from said database and to determine, based on the activity profile of the player and on the motion profile of the equipment and on the additional information retrieved from the database, the one of a plurality of game scenarios involving the player and the equipment.

5. The system of claim 1, wherein the system comprises a further player module being attachable to a further player, wherein the computing unit is configured to receive further player based data from the further player module, the further player based data representing a further activity profile of the further player, wherein the computing unit is configured to determine, based on the activity profile of the player and on the further activity profile of the further player and on the motion profile of the equipment, one of a plurality of game scenarios involving the player and the further player and the equipment.

6. The system of claim 1, wherein the system further comprises at least one infrastructure module being associated with a playing field where the sports game takes place and/or being associated with an installation belonging to said playing field, the infrastructure module being arranged inside, outside, at, on, over, under or around the playing field and/or inside, outside, at, on, over, under or around said installation of said playing field, wherein the computing unit is configured to receive infrastructure based data from the infrastructure module and to determine, based on the activity profile of the player and on the motion profile of the equipment and on the infrastructure based data, the one of a plurality of game scenarios involving the player and the equipment.

7. The system of claim 6, wherein the infrastructure module comprises a directional antenna being directed onto the playing field, and/or being directed parallel or orthogonal to a spatially nearest one of demarcation lines of the playing field, and/or being directed along a demarcation line of the playing field.

8. The system of claim 6, wherein the infrastructure module is configured to measure a Received Signal Strength Indication—RSSI—value of a signal received from the player module and/or from the equipment module, and/or wherein at least one of the player module and the equipment module is configured to measure a Received Signal Strength Indication—RSSI—value of a signal received from the infrastructure module, and wherein at least one of the infrastructure module, the player module, the equipment module and the computing unit is configured to calculate based on the measured RSSI value a relative spatial distance between the infrastructure module and at least one of the player module and the equipment module, and/or a relative spatial distance between at least one of the player module and the equipment module on the playing field, and/or an absolute position of the player module and/or the equipment module on the playing field.

9. The system of claim 1, wherein the player module is configured to measure a Received Signal Strength Indication—RSSI—value of a signal received from the equipment module and/or wherein the equipment module is configured to measure a Received Signal Strength Indication—RSSI—value of a signal received from the player module, and wherein at least one of the player module, the equipment module and the computing unit is configured to calculate based on the measured RSSI value a relative spatial distance between the player module and the equipment module, and/or an absolute position of the player module and the equipment module on a playing field.

10. The system of claim 1, wherein the computing unit is configured to receive an RSSI value from at least one of the player module and the equipment module, and to determine, based on the activity profile of the player and on the motion profile of the equipment and on the received RSSI value, the one of a plurality of game scenarios involving the player and the equipment.

11. The system of claim 9, wherein the computing unit is configured to receive a first RSSI value being associated with a first player module and a second RSSI value being associated with a second player module, wherein the computing unit is further configured to compare the first and the second RSSI values and to take the player based data of the first player module if a result of comparing the RSSI values indicates that the first player module comprises a lower spatial distance to the equipment than the second player module.

12. A method for determining a game scenario in a sports game, the method comprising receiving player based data from a player module being attached to a player, the player based data representing an activity profile of the player, receiving equipment based data from an equipment module being attached to a sports equipment to be used in said sports game, the equipment based data representing a motion profile of the equipment, wherein receiving player based data from the player module comprises receiving raw measurement data from a player sensor device comprised by the player module, the raw measurement data being associated with the player to which the player module is attached, and performing a feature extraction of the raw measurement data for determining, based on one or more extracted features, one or more physical events being executable by the player, determining the activity profile of the player based on the extracted one or more features and/or based on the determined one or more physical events and transmitting the activity profile as the player based data to a computing unit, and/or transmitting the extracted one or more features and/or the determined one or more physical events to the computing unit for determining the activity profile of the player, wherein receiving equipment based data from the equipment module comprises receiving raw measurement data from an equipment sensor device comprised by the equipment module, the raw measurement data being associated with the equipment to which the equipment module is attached, and performing a feature extraction of the raw measurement data for determining, based on one or more extracted features, one or more physical events being executable by or exertable on the equipment, determining the motion profile of the equipment based on a plurality of consecutive features and/or based on a plurality of consecutive physical events, and transmitting the motion profile as the equipment based data to the computing unit, and/or transmitting the plurality of consecutive features and/or the plurality of consecutive physical events to the computing unit for determining the motion profile of the equipment, determining the player based data during a predetermined time window, and determining the equipment based data during a predetermined time window, and timely synchronizing the received player based data and the received equipment based data such that the time windows of the player based data and of the equipment based data at least partially overlap in a time domain, and combining the activity profile of the player with the motion profile of the equipment so as to classify the activity profile of the player and the motion profile of the equipment into one of a plurality of game scenarios involving the player and the equipment.

13. A non-transitory computer readable storage medium having a computer program stored thereon to perform a method for determining a game scenario in a sports game, the method comprising receiving player based data from a player module being attached to a player, the player based data representing an activity profile of the player, receiving equipment based data from an equipment module being attached to a sports equipment to be used in said sports game, the equipment based data representing a motion profile of the equipment, wherein receiving player based data from the player module comprises receiving raw measurement data from a player sensor device comprised by the player module, the raw measurement data being associated with the player to which the player module is attached, and performing a feature extraction of the raw measurement data for determining, based on one or more extracted features, one or more physical events being executable by the player, determining the activity profile of the player based on the extracted one or more features and/or based on the determined one or more physical events, and transmitting the activity profile as the player based data to a computing unit, and/or transmitting the extracted one or more features and/or the determined one or more physical events to the computing unit for determining the activity profile of the player, wherein receiving equipment based data from the equipment module comprises receiving raw measurement data from an equipment sensor device comprised by the equipment module, the raw measurement data being associated with the equipment to which the equipment module is attached, and performing a feature extraction of the raw measurement data for determining, based on one or more extracted features, one or more physical events being executable by or executable on the equipment, determining the motion profile of the equipment based on a plurality of consecutive features and/or based on a plurality of consecutive physical events and transmitting the motion profile as the equipment based data to the computing unit, and/or transmitting the plurality of consecutive features and/or the plurality of consecutive physical events to the computing unit for determining the motion profile of the equipment, and determining the player based data during a predetermined time window, and determining the equipment based data during a predetermined time window, and timely synchronizing the received player based data and the received equipment based data such that the time windows of the player based data and of the equipment based data at least partially overlap in a time domain, and combining the activity profile of the player with the motion profile of the equipment so as to classify the activity profile of the player and the motion profile of the equipment into one of a plurality of game scenarios involving the player and the equipment, when said computer program is run by a computer.

* * * * *